(12) United States Patent
Endo et al.

(10) Patent No.: US 7,405,346 B2
(45) Date of Patent: Jul. 29, 2008

(54) GENE CAPABLE OF IMPARTING SALT STRESS RESISTANCE

(75) Inventors: Noboru Endo, Tokyo (JP); Kouki Yoshida, Tokyo (JP); Miho Akiyoshi, Tokyo (JP); Yasuko Yoshida, Tokyo (JP); Chieko Ohsumi, Kanagawa (JP); Daisuke Igarashi, Kanagawa (JP)

(73) Assignees: Taisei Corporation, Tokyo (JP); Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/553,124

(22) PCT Filed: Apr. 15, 2004

(86) PCT No.: PCT/JP2004/005403

§ 371 (c)(1),
(2), (4) Date: Oct. 14, 2005

(87) PCT Pub. No.: WO2004/092372

PCT Pub. Date: Oct. 28, 2004

(65) Prior Publication Data

US 2007/0028332 A1    Feb. 1, 2007

(30) Foreign Application Priority Data

Apr. 17, 2003 (JP) ............................ 2003-113194
Mar. 17, 2004 (JP) ............................ 2004-075932

(51) Int. Cl.
*A01H 5/00* (2006.01)
*C12N 5/14* (2006.01)
*C12N 15/82* (2006.01)
*C12N 15/29* (2006.01)
*C07H 21/04* (2006.01)

(52) U.S. Cl. ................ 800/295; 435/320.1; 435/419; 435/468; 536/23.2; 536/23.6; 800/278; 800/306; 800/320

(58) Field of Classification Search ............ None
See application file for complete search history.

(56) References Cited

U.S. PATENT DOCUMENTS

2004/0214272 A1 * 10/2004 La Rosa et al. ............ 435/69.1

FOREIGN PATENT DOCUMENTS

WO    WO 91/06651    5/1991

OTHER PUBLICATIONS

Town et al. (NCBI, GenBank, Sequence Accession No. NM_101148, Published Aug. 20, 2002).*
Keskin et al. (Protein Science, 13:1043-1055, 2004).*
Guo et al. (PNAS, 101: 9205-9210, 2004).*
Thornton et al. (Nature structural Biology, structural genomics supplement, Nov. 2000).*
Dormann et al. (The Plant Journal, 13:641-652, 1998).*
K. B. Marcum et al., "Growth responses, ion relations, and osmotic adaptations of eleven $C_4$ Turfgrasses to salinity", Agronomy Journal, vol. 82, No. 5, pp. 892-896 1990.
M. Akiyoshi et al., "Diversity of salt tolerance among the gramineae subfamily 5) single gene transfer improved the practical level of salt tolerance in rice", Breeding Research, Japanese Society of Breeding, vol. 5, suppl. 2, p. 323 (with English translation of summary) 2003.
K.B. Marcum et al., "Growth responses, ion relations, and osmotic adaptations of eleven C. Turfgrasses to salinity", AGRONOMY JOURNAL, vol. 82, No. 5, pp. 892-896.
M. Akiyoshi et al., "Diversity of salt tolerance among the gramineae subfamily 5) single gene transfer improved the practical level of salt tolerance in rice", BREEDING RESEARCH, Japanese Society of Breeding, vol. 5, suppl. 2, p. 323 (with English translation of summary).

* cited by examiner

*Primary Examiner*—David H. Kruse
*Assistant Examiner*—Vinod Kumar
(74) *Attorney, Agent, or Firm*—Oblon, Spivak, McClelland, Maier & Neustadt, P.C.

(57) ABSTRACT

This invention provides a novel gene that can impart salt stress tolerance to plants for a long period of time and salt stress tolerant transgenic plants to which such gene has been introduced. Such novel gene encodes the following protein (a), (b), or (c), and such salt stress tolerant transgenic plant has such gene introduced therein: (a) a protein consisting of the amino acid sequence as shown in SEQ ID NO: 2 in the Sequence Listing; (b) a protein consisting of an amino acid sequence derived from the amino acid sequence as shown in SEQ ID NO: 2 in the Sequence Listing by deletion, substitution, or addition of one or several amino acid residues and having activity of imparting salt stress tolerance to plants; or (c) a protein consisting of an amino acid sequence derived from the amino acid sequence as shown in SEQ ID NO: 2 in the Sequence Listing by deletion, substitution, or addition of one or several amino acid residues and having UDP-glucose 4-epimerase activity.

27 Claims, 20 Drawing Sheets

Fig.2
A
NaCl concentration
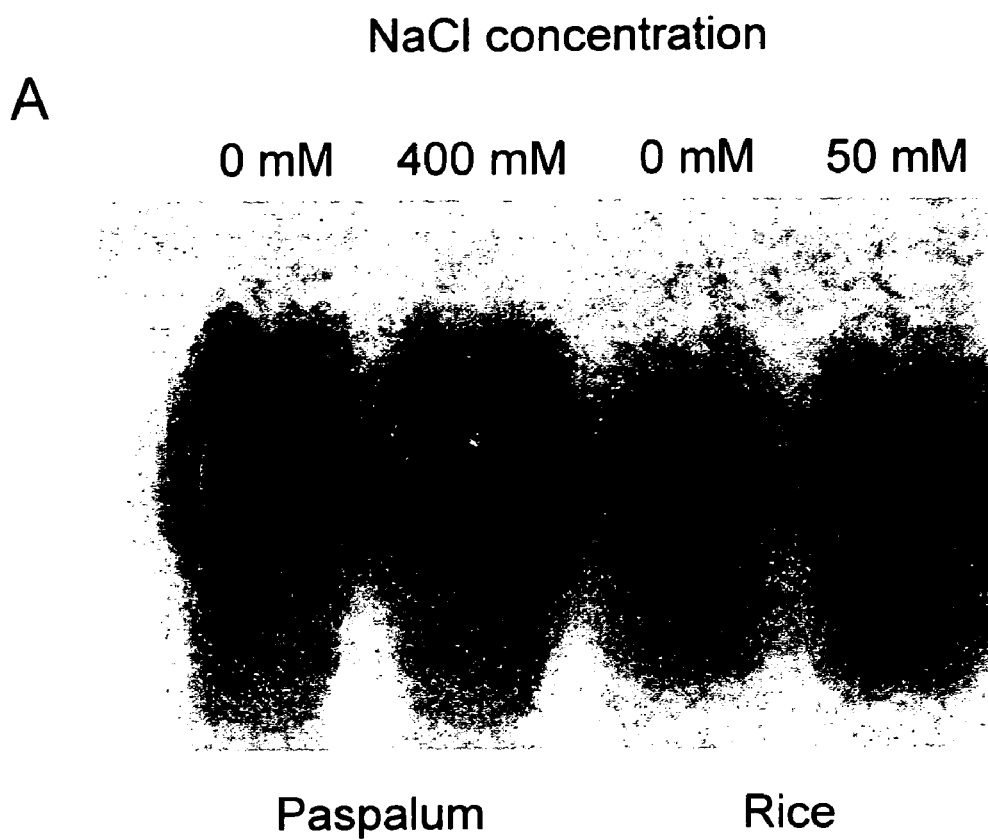
0 mM    400 mM    0 mM    50 mM
Paspalum                Rice
B
NaCl concentration
0 mM    400 mM    0 mM    50 mM
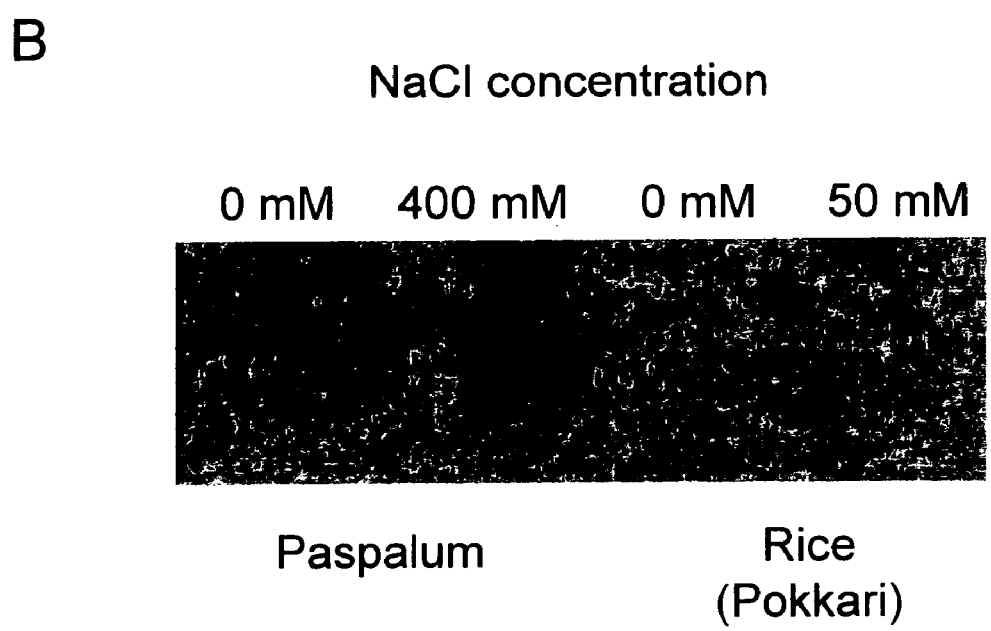
Paspalum                Rice
(Pokkari)

Fig.4

```
[GENETYX-MAC: Multiple Alignment]
Date       : 2003.03.16

Ps UGE1      1  MAIGGAEAGGGGAEAEGR-SVLVTGGAGFIGTHTALALLEDGYGMTVVDNFHNSVPEALE   59
PsUGE2       1  ------------MVSAVLRTIL-VTGGAGYIGSHTVLLLQDGFRMVVVDNLDNASDVALA   48
At1g12780    1  ------------MGSSVEQNILVTGGAGFIGTHTVVQLLKDGFKMSIIDNFDNSVIEAVD   48
At1g63180    1  ------------MGSSVEQNILVTGGAGFIGTHTVVQLLNDGFKMTIIDNLDNSVVEAVH   48
Ct UGE       1  ------MVS-SRMABGET--ILVTGGAGFIGSHTVVQLLKDGFHVSLIDNLVNSVIDAVH   51

Ps UGE1     60  RVR-DIADPALS-AR-DDAIRGDLASAGDLEKAFAARAVDAVVHFAGLKAVGESVARADM  116
PsUGE2      49  RVAQLAAS-SNGGAANLVAHKVDLADRHALEDIFSSHAFEAVIHFAGLKAVGESVQKPLL  107
At1g12780   49  RVR-ELVGPDLS-KK-LDFNLGDLRNKGDIEKLFSKQAFDAVIHFAGLKAVGESVGNPAA  105
At1g63180   49  RVR-ELVGPDLS-TK-LEFNLGDLRNKGDIEKLFSNQAFDAVIHFAGLKAVGESVGNPAA  105
Ct UGE      52  RVR-LLVGPALS-SN-LHFHHGDLRNIHDLDILFSKTKFDAVIHFAGLKGVGESVLNPSN  108

Ps UGE1    117  YYENNLAGTINLVKAFNEHGCKKMVFSSSATVYGLPEVLPCVEDSKDAANPYGRTKLID  176
PsUGE2     108  YYDNNLIGTITLLEVMAAHGCKKLVFSSSATVYGWPKEVPQTEEFPLCATNPYGRTKLVI  167
At1g12780  106  YFDNNLVGTINLYETMAKVNCKMMVFSSSATVYGQPEKLPQMEDFELKAMNPYGRTKLFL  165
At1g63180  106  YFDNNLVGTINLYETMAKVNCKMMVFSSSATVYGQPEIVPCVEDFELQAMNPYGRTKLFL  165
Ct UGE     109  YYDNNLVATINLFQVMSKFNCKKLMISSSATVYGQPDQLPCVEDSNLHAMNPYGRSKLFV  168

Ps UGE1    177  EELARDVLRADPGHSIVLLRYFNPILGAHSBGEIGEDPKGVPNNLLPYIQQVAVGRLPELN  236
PsUGE2     168  EDICRDVHASDPDHKIILLRYFNPVGAHPBGHIGEDPSBIPNNLMPVVQQVAVGRAPHLT  227
At1g12780  166  EEIARDIQKREPEWRIILLRYFNPVGAHESGSIGEDPKGIPNNLMPVIQQVAVGRLPELN  225
At1g63180  166  EEIARDIHAREPEWKIILLRYFNPVGAHESGRIGEDPKGIPNNLMPVIQQVAVGRLPELN  225
Ct UGE     169  EEMARDIQRAEREWRIILLRYFNPVGAHESGQIGEDPRGLPNNLMPVIQQVAVARLPELN  228

Ps UGE1    237  VYGHDYPTRDGTAIRDYIHVVDLADGHIAALNKLEDTPDF-GCVAVNLGTGRGTSVLEMV  295
PsUGE2     228  VYGTDYNIKDGTGPRDYIHVVDLADGHIAALGKLYEDSDRIGCEVVNLGTGKGTSVLEMV  287
At1g12780  226  VYGHDYPTEDGSAVRDYIHVMDLADGHIAALRKLFADPKIT-GCTAVNLGTGQGTSVLEMV  284
At1g63180  226  VFGHDYPTMDGSAVRDYIHVMDLADGHIAALNKLFSDSKII-GCTAVNLGTGQGTSVLEMV  284
Ct UGE     229  IPGHDYPTKDGTAIRDYIHVMDLADGHIAALRKLFTTDNLI-GCTAVNLGTGRGTSVLEMV  287

Ps UGE1    296  AAFKKASGKEIPTKMCPRRPGDATEVYASTEKAEAELGWRQPGIEEMCRDQWNWAKKNP  355
PsUGE2     288  AAFEKVBGKKIPLVLAGRAPGDAEIVYARTAKAEEKELKWKAKYGIEEMCRDQWNWASKNP  347
At1g12780  285  AAFEKASGKKIPIKLCPRRSGDATAVYASTEKAEEKELGWKAKYGVDEMCRDQLKLANNP  344
At1g63180  285  SSFEKASGKKIPIKLCPRRAGDATAVYASTQKAEEKELGWKAKYGVDEMCRDQWNWANKNP  344
Ct UGE     288  AAFEKASGKKIPIKMCPRRPGDATAVYASTEKAEEKELGWKAKYGVEEMCRDQLKWASNNP  347

Ps UGE1    356  VGVCBTAEK--                                                   364
PsUGE2     348  YGVAGSPDNSS                                                   358
At1g12780  345  WGYQKL----                                                    351
At1g63180  345  WGFDKKP---                                                    351
Ct UGE     348  WGYCGKH---                                                    354
```

1  2  3  4  5  6  7

Fig.7
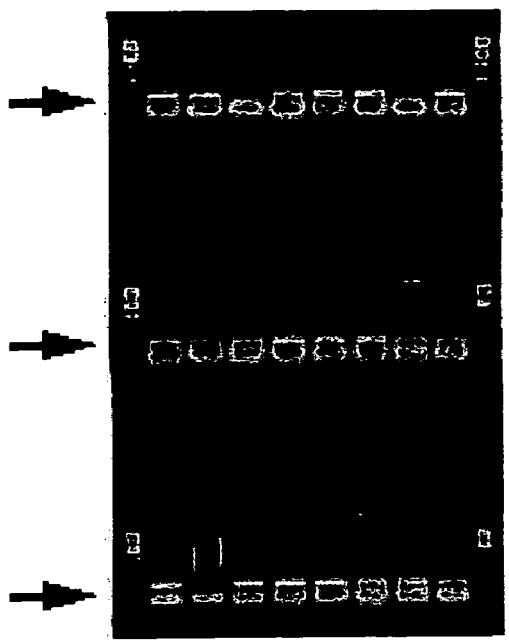
VNT
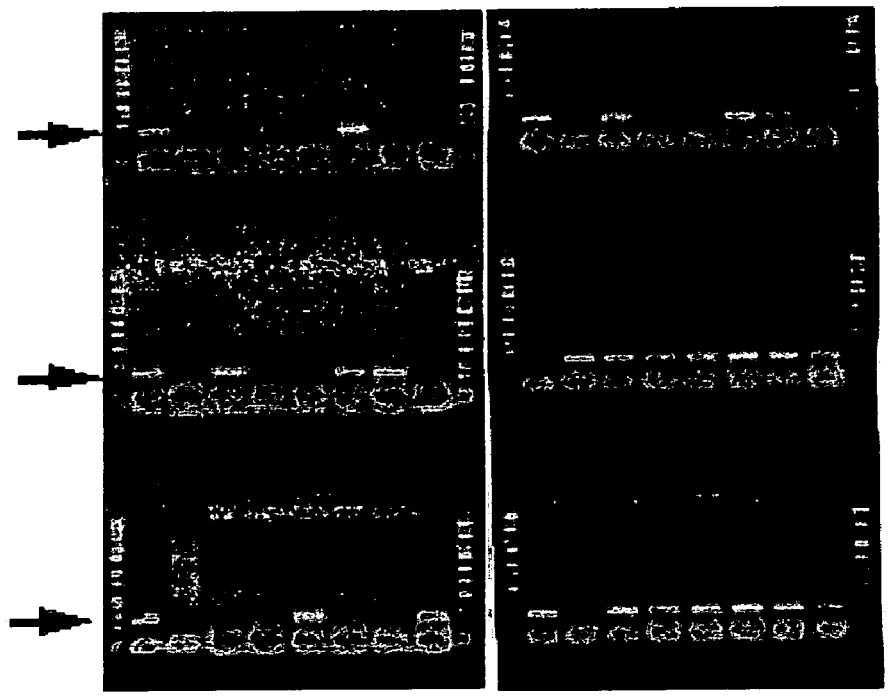
V NT

Fig.11
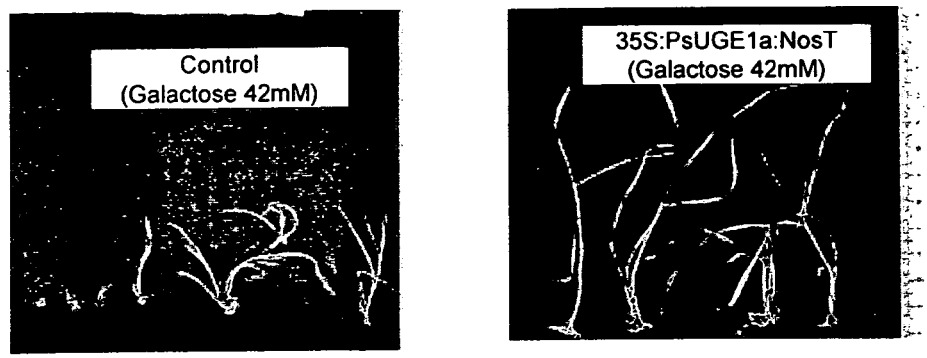
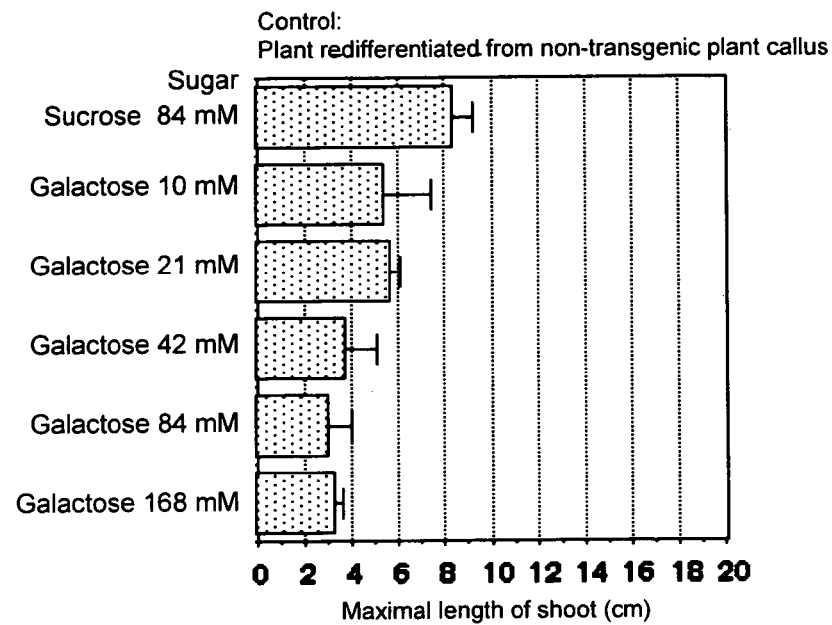
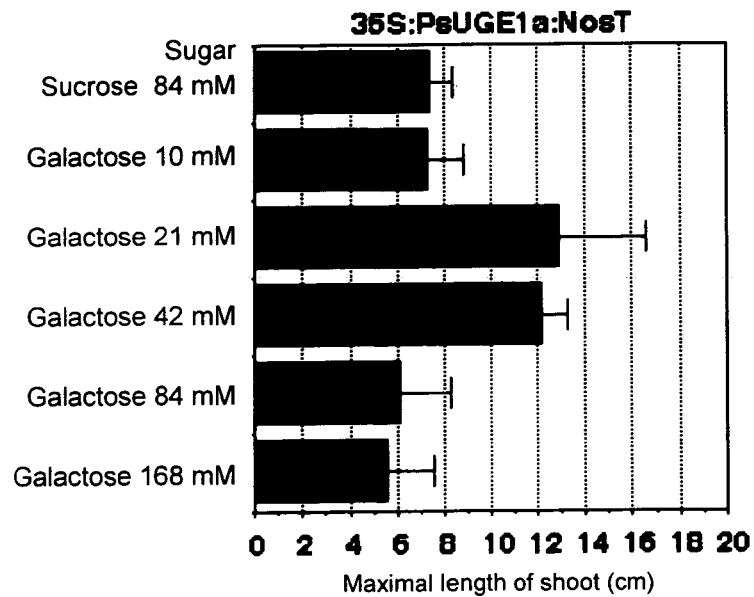

Fig.14
Non-transgenic rice (2 weeks later)
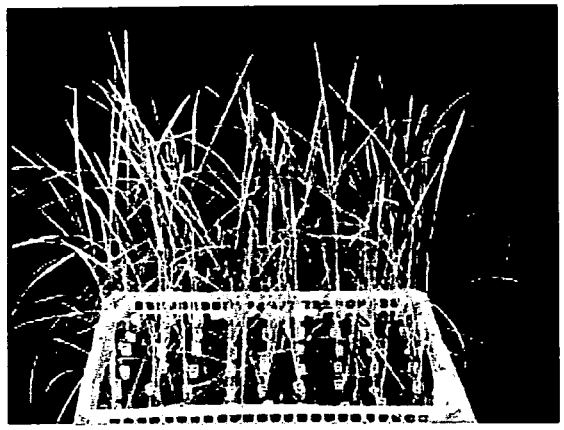
PseUGE transgenic rice ( 2 weeks later)
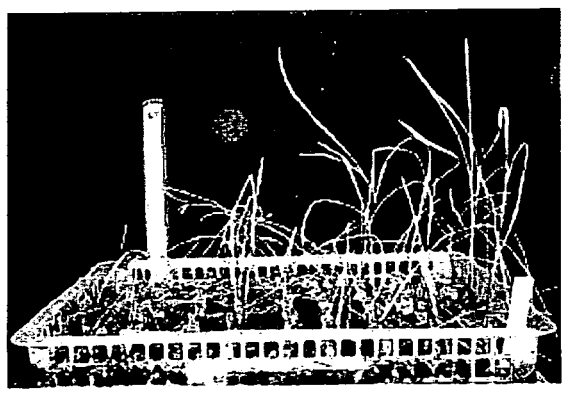
Non-transgenic rice (4 weeks leter)
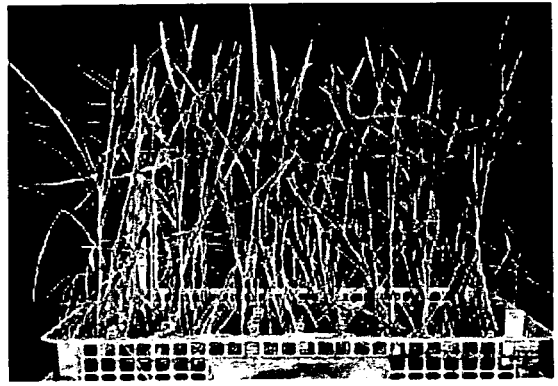
PseUGE transgenic rice (4 weeks later)
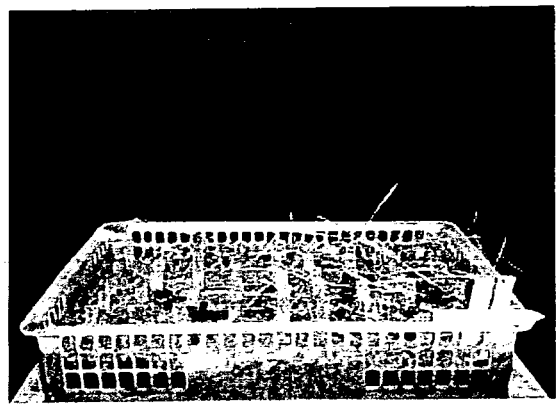
Non-transgenic rice (8 weeks leter)
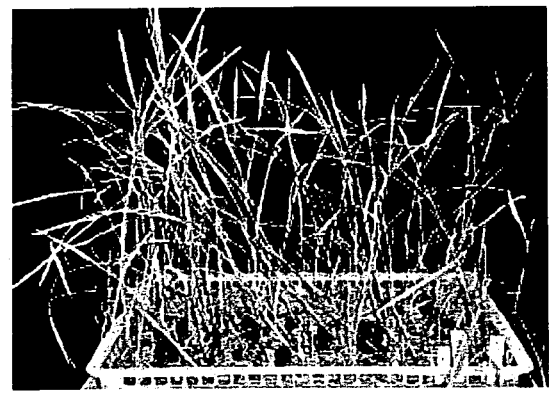
PseUGE transgenic rice (8 weeks later)

```
                              SEQUENCE LISTING

<160> NUMBER OF SEQ ID NOS: 17

<210> SEQ ID NO 1
<211> LENGTH: 1554
<212> TYPE: DNA
<213> ORGANISM: Seashore Paspalum
<220> FEATURE:
<221> NAME/KEY: CDS
<222> LOCATION: (131)..(1222)

<400> SEQUENCE: 1
ggcacgagga gcgccgccgc cggttgccag acactgccag tgcaacagag ccgcaaaacc     60
acacgccccc tcgcgcgctc acacagagag agacacacac atcgatcgag cggccggccg    120
gacggcgcag atg gcg atc ggc ggg gcg gag gcc ggc ggg gga ggc gcg        169
            Met Ala Ile Gly Gly Ala Glu Ala Gly Gly Gly Gly Ala
              1               5                  10 ggg gcc agc ggc cgg agc gtg ctg gtg acg ggc ggc gcg ggg ttc atc       217
Gly Ala Ser Gly Arg Ser Val Leu Val Thr Gly Gly Ala Gly Phe Ile
 15                  20                  25 ggc acg cac acg gcg ctg cgc ctg ctg gag cag ggc tac ggc gtc acc       265
Gly Thr His Thr Ala Leu Arg Leu Leu Glu Gln Gly Tyr Gly Val Thr
 30                  35                  40                  45 gtc gtc gac aac ttc cac aac tcc gtc ccc gag gcg ctc gaa cgc gtc       313
Val Val Asp Asn Phe His Asn Ser Val Pro Glu Ala Leu Glu Arg Val
                 50                  55                  60 cgc ctc atc gcc ggg ccc gcg ctc tcc gcc cgc ctc gac ttc atc cgg       361
Arg Leu Ile Ala Gly Pro Ala Leu Ser Ala Arg Leu Asp Phe Ile Arg
             65                  70                  75 ggg gat ctg agg agc gcc ggg gac ttg gag aag gcg ttc gcg gcc agg       409
Gly Asp Leu Arg Ser Ala Gly Asp Leu Glu Lys Ala Phe Ala Ala Arg
         80                  85                  90 agg tac gac gcc gtc gtc cac ttc gcg ggg ctc aag gcc gtc ggg gag       457
Arg Tyr Asp Ala Val Val His Phe Ala Gly Leu Lys Ala Val Gly Glu
     95                 100                 105 agc gtc gcg cgc ccg gac atg tac tac gag aac aac ctc gcc ggc acc       505
Ser Val Ala Arg Pro Asp Met Tyr Tyr Glu Asn Asn Leu Ala Gly Thr
110                 115                 120                 125 atc aac ctc tac aag gcc atg aac gag cac ggc tgc aag aag atg gtg       553
Ile Asn Leu Tyr Lys Ala Met Asn Glu His Gly Cys Lys Lys Met Val
                130                 135                 140 ttc tcg tcg tcc gcg acc gtg tac ggc tgg ccg gag gtg atc ccg tgc       601
Phe Ser Ser Ser Ala Thr Val Tyr Gly Trp Pro Glu Val Ile Pro Cys
            145                 150                 155
```

-continued

| | | |
|---|---|---|
| gtc gag gac tcc aag ctg cag gcc gcc aac ccc tac ggc agg acc aag<br>Val Glu Asp Ser Lys Leu Gln Ala Ala Asn Pro Tyr Gly Arg Thr Lys<br>    160                          165                          170 | 649 | |

```
gtc gag gac tcc aag ctg cag gcc gcc aac ccc tac ggc agg acc aag    649
Val Glu Asp Ser Lys Leu Gln Ala Ala Asn Pro Tyr Gly Arg Thr Lys
        160                 165                 170 ctc atc ctg gag gag ttg gcg cgg gac tac cag cgc gcg gac ccg ggc    697
Leu Ile Leu Glu Glu Leu Ala Arg Asp Tyr Gln Arg Ala Asp Pro Gly
    175                 180                 185 tgg agc atc gtc ctg ctg cgc tac ttc aac ccc atc ggc gcc cac agc    745
Trp Ser Ile Val Leu Leu Arg Tyr Phe Asn Pro Ile Gly Ala His Ser
190                 195                 200                 205 tcc ggc gag atc ggc gag gac ccc aag ggg gtg ccc aac aac ctg ctg    793
Ser Gly Glu Ile Gly Glu Asp Pro Lys Gly Val Pro Asn Asn Leu Leu
                210                 215                 220 ccc tac atc cag cag gtc gcc gtc ggc agg ctc ccc gag ctc aac gtc    841
Pro Tyr Ile Gln Gln Val Ala Val Gly Arg Leu Pro Glu Leu Asn Val
            225                 230                 235 tac ggc cac gat tac ccc acc cgt gac ggc acc gcg atc agg gac tac    889
Tyr Gly His Asp Tyr Pro Thr Arg Asp Gly Thr Ala Ile Arg Asp Tyr
        240                 245                 250 ata cac gtc gtc gac ctg gcc gac ggg cac atc gcg gcg ctg aac aag    937
Ile His Val Val Asp Leu Ala Asp Gly His Ile Ala Ala Leu Asn Lys
    255                 260                 265 ctg ttc gac act cct gat ttc ggt tgt gtg gcc tac aat ctg ggc aca    985
Leu Phe Asp Thr Pro Asp Phe Gly Cys Val Ala Tyr Asn Leu Gly Thr
270                 275                 280                 285 ggg cgc ggc aca tcc gtt ctc gag atg gtg gcg gcg ttc aag aag gca   1033
Gly Arg Gly Thr Ser Val Leu Glu Met Val Ala Ala Phe Lys Lys Ala
                290                 295                 300 tcc ggc aag gag atc ccc acc aag atg tgc ccc agg aga ccg ggt gac   1081
Ser Gly Lys Glu Ile Pro Thr Lys Met Cys Pro Arg Arg Pro Gly Asp
            305                 310                 315 gcg acg gag gtt tac gcg tcc act gag aag gcc gaa agg gag ctc gga   1129
Ala Thr Glu Val Tyr Ala Ser Thr Glu Lys Ala Glu Arg Glu Leu Gly
        320                 325                 330 tgg agg gcc cag tat gga atc gag gag atg tgc agg gac cag tgg aac   1177
Trp Arg Ala Gln Tyr Gly Ile Glu Glu Met Cys Arg Asp Gln Trp Asn
    335                 340                 345 tgg gcc aag aag aac ccc tat ggc tac tgc ggc act gcc gaa aaa       1222
Trp Ala Lys Lys Asn Pro Tyr Gly Tyr Cys Gly Thr Ala Glu Lys
350                 355                 360 tagagcgcgt gcattaatca gatctctgga ctgaatttgt ccatggttga tggttgtctc  1282
agacctatcg gtggaagatg taacaagtag agaccgctcg aatgtgccta gctacgaaag  1342
tttcgtacca tctctcttgt cataacctca tgtagatggc cattttattg gaattagcct  1402
tagccttcag gcccggcgct gttagccatt gcttgctatc gaggtaggtg gggttggaac  1462
tttgggcgcc cttgaacttc cattatcatc attcgcacag acggcacagt tgcgcagtga  1522
gccgttgact gcttgtgaaa aaaaaaaaa aa                                1554
```

<210> SEQ ID NO 2
<211> LENGTH: 364
<212> TYPE: PRT
<213> ORGANISM: Seashore Paspalum

<400> SEQUENCE: 2

Met Ala Ile Gly Gly Ala Glu Ala Gly Gly Gly Gly Ala Gly Ala Ser
1               5                   10                  15

Gly Arg Ser Val Leu Val Thr Gly Gly Ala Gly Phe Ile Gly Thr His
                20                  25                  30

Thr Ala Leu Arg Leu Leu Glu Gln Gly Tyr Gly Val Thr Val Val Asp

-continued

```
                35                  40                  45
Asn Phe His Asn Ser Val Pro Glu Ala Leu Glu Arg Val Arg Leu Ile
 50                  55                  60
Ala Gly Pro Ala Leu Ser Ala Arg Leu Asp Phe Ile Arg Gly Asp Leu
 65                  70                  75                  80
Arg Ser Ala Gly Asp Leu Glu Lys Ala Phe Ala Arg Arg Tyr Asp
                 85                  90                  95
Ala Val Val His Phe Ala Gly Leu Lys Ala Val Gly Glu Ser Val Ala
                100                 105                 110
Arg Pro Asp Met Tyr Tyr Glu Asn Asn Leu Ala Gly Thr Ile Asn Leu
                115                 120                 125
Tyr Lys Ala Met Asn Glu His Gly Cys Lys Lys Met Val Phe Ser Ser
                130                 135                 140
Ser Ala Thr Val Tyr Gly Trp Pro Glu Val Ile Pro Cys Val Glu Asp
145                 150                 155                 160
Ser Lys Leu Gln Ala Ala Asn Pro Tyr Gly Arg Thr Lys Leu Ile Leu
                165                 170                 175
Glu Glu Leu Ala Arg Asp Tyr Gln Arg Ala Asp Pro Gly Trp Ser Ile
                180                 185                 190
Val Leu Leu Arg Tyr Phe Asn Pro Ile Gly Ala His Ser Ser Gly Glu
                195                 200                 205
Ile Gly Glu Asp Pro Lys Gly Val Pro Asn Asn Leu Leu Pro Tyr Ile
                210                 215                 220
Gln Gln Val Ala Val Gly Arg Leu Pro Glu Leu Asn Val Tyr Gly His
225                 230                 235                 240
Asp Tyr Pro Thr Arg Asp Gly Thr Ala Ile Arg Asp Tyr Ile His Val
                245                 250                 255
Val Asp Leu Ala Asp Gly His Ile Ala Ala Leu Asn Lys Leu Phe Asp
                260                 265                 270
Thr Pro Asp Phe Gly Cys Val Ala Tyr Asn Leu Gly Thr Gly Arg Gly
                275                 280                 285
Thr Ser Val Leu Glu Met Val Ala Ala Phe Lys Lys Ala Ser Gly Lys
                290                 295                 300
Glu Ile Pro Thr Lys Met Cys Pro Arg Arg Pro Gly Asp Ala Thr Glu
305                 310                 315                 320
Val Tyr Ala Ser Thr Glu Lys Ala Glu Arg Glu Leu Gly Trp Arg Ala
                325                 330                 335
Gln Tyr Gly Ile Glu Glu Met Cys Arg Asp Gln Trp Asn Trp Ala Lys
                340                 345                 350
Lys Asn Pro Tyr Gly Tyr Cys Gly Thr Ala Glu Lys
                355                 360
```

<210> SEQ ID NO 3
<211> LENGTH: 23
<212> TYPE: DNA
<213> ORGANISM: Artificial Sequence
<220> FEATURE:
<223> OTHER INFORMATION: Synthetic DNA

<400> SEQUENCE: 3
ggtgcgacga ctcctggagc ccg                                           23

<210> SEQ ID NO 4
<211> LENGTH: 24
<212> TYPE: DNA
<213> ORGANISM: Artificial Sequence

```
<220> FEATURE:
<223> OTHER INFORMATION: Synthetic DNA

<400> SEQUENCE: 4
ttgacaccag accaactggt aatg                                              24

<210> SEQ ID NO 5
<211> LENGTH: 339
<212> TYPE: DNA
<213> ORGANISM: Artificial Sequence
<220> FEATURE:
<223> OTHER INFORMATION: Synthetic DNA

<400> SEQUENCE: 5
tgccgtgggc tccggcgggt tcgccttcca cgagcaccac gagaagaagg aggaccacaa        60
ggacgccgag gaggccggcg gcgagaagaa gcaccacttc ttcggctgat ccatctcacc       120
atctccatct cccacccccca tcgatccatt tgtgttggct ttaattccct gcgtgcatgc      180
gtgttgttga ataaggggcc ggttccatct gtacgtacgt gtactccgag acctatcgtc       240
atgtgtgtgt gtgtacgtat acctgctgtg tacatgatgg tcgtatatgc cactggacta      300
tgtgtgtgtg caactctgtt ctgatttgct atatataag                              339

<210> SEQ ID NO 6
<211> LENGTH: 497
<212> TYPE: DNA
<213> ORGANISM: Seashore Paspalum

<400> SEQUENCE: 6
tgcagggacc agtggaactg ggccaagaag aaccctatg gctactgcgg cactgccgaa        60
aaatagagcg cgtgcattaa tcagatctct ggactgaatt tgtccatggt tgatggttgt      120
ctcagaccta tcggtggaag atgtaacaag tagagaccgc tcgaatgtgc ctagctacga      180
agtttcgtac catctctctt gtcataacct catgtagatg gtcattttat tggaattagc      240
cttagccttc aggcccggcg ctgttaaaat ttgttttaca catggatttt ctcgctacgt      300
gtgatacata ttgtgtctgt aataatcctg atcggagttt ccagtaataa aaccgatcca      360
cgacggtggc tacgccctgt gttgtagtac tgtgaatatg atgtggtaat aacaataact      420
tgcagtgaga cttcagcttt caaaaaaaaa aaaaaaaaaa aaaaaaaaaa aaaaaaaaaa      480
aaaaaaaaaa aaaaaaa                                                     497

<210> SEQ ID NO 7
<211> LENGTH: 396
<212> TYPE: DNA
<213> ORGANISM: Artificial Sequence
<220> FEATURE:
<223> OTHER INFORMATION: Synthetic DNA

<400> SEQUENCE: 7
ggccgctgtg cagggaccag tggaactggg ccaagaagaa ccctatggc tactgcggca        60 ctgccgaaaa atagagcgcg tgcattaatc agatctctgg actgaatttg tccatggttg      120
atggttgtct cagacctatc ggtggaagat gtaacaagta gagaccgctc gaatgtgcct      180
agctacgaag tttcgtacca tctctcttgt cataacctca tgtagatggt cattttattg      240
gaattagcct tagccttcag gcccggcgct gttaaaattt gttttacaca tggattttct      300
cgctacgtgt gatacatatt gtgtctgtaa taatcctgat cggagtttcc agtaataaaa      360
ccgatccacg acggtggcta cgccctgtgt tgtagt                                396
```

<210> SEQ ID NO 8
<211> LENGTH: 1540
<212> TYPE: DNA
<213> ORGANISM: Seashore Paspalum
<220> FEATURE:
<221> NAME/KEY: CDS
<222> LOCATION: (110)..(1183)

<400> SEQUENCE: 8

```
ggcacgaggg agagattgag aggaaatcga gttcatcctc cctccaccat cgccgatcat      60
agccttccct tccccgatcg ccgatccgat ccacaagcaa gcagccagg atg gtt tct     118
                                                       Met Val Ser
                                                         1 gcg gtg ctt cgt acc atc ctt gtg acg ggc ggc gcc ggc tac atc ggc      166
Ala Val Leu Arg Thr Ile Leu Val Thr Gly Gly Ala Gly Tyr Ile Gly
      5                  10                  15 agc cac acc gtg ctg ctg ctg cag cag gga ttc cgc gtc gtc gtc          214
Ser His Thr Val Leu Leu Leu Gln Gln Gly Phe Arg Val Val Val
 20                  25                  30                  35 gtc gac aac ctc gac aac gcc tcc gac gtc gcg ctc gcc cgc gtc gcg      262
Val Asp Asn Leu Asp Asn Ala Ser Asp Val Ala Leu Ala Arg Val Ala
                 40                  45                  50 cag ctc gca gca agc agc aac ggc ggc gcc gcc aac ctc gtc ttc cac      310
Gln Leu Ala Ala Ser Ser Asn Gly Gly Ala Ala Asn Leu Val Phe His
         55                  60                  65 aag gtt gac ctt cgc gac agg cac gcg ctg gag gac atc ttc tcc tcc      358
Lys Val Asp Leu Arg Asp Arg His Ala Leu Glu Asp Ile Phe Ser Ser
 70                  75                  80 cac agg ttt gag gct gtg att cat ttt gct ggg ctc aaa gct gtt ggc      406
His Arg Phe Glu Ala Val Ile His Phe Ala Gly Leu Lys Ala Val Gly
         85                  90                  95 gag agc gtg cag aag ccg ctg ctt tac tac gac aac aac ctc atc ggc      454
Glu Ser Val Gln Lys Pro Leu Leu Tyr Tyr Asp Asn Asn Leu Ile Gly
100                 105                 110                 115 acc atc acc ctc ctc gag gtc atg gcc gca cat ggc tgc aag aag ctg      502
Thr Ile Thr Leu Leu Glu Val Met Ala Ala His Gly Cys Lys Lys Leu
                120                 125                 130 gtg ttc tcg tca tct gca act gtc tat ggg tgg ccc aag gaa gtg cca      550
Val Phe Ser Ser Ser Ala Thr Val Tyr Gly Trp Pro Lys Glu Val Pro
        135                 140                 145 tgc acc gaa gaa ttc cct ctt tgc gcc acc aac ccc tat ggg cga acc      598
Cys Thr Glu Glu Phe Pro Leu Cys Ala Thr Asn Pro Tyr Gly Arg Thr
    150                 155                 160 aag ctt gtg att gaa gat atc tgc cgc gac gtc cac cgt tca gac cct      646
Lys Leu Val Ile Glu Asp Ile Cys Arg Asp Val His Arg Ser Asp Pro
165                 170                 175 gat tgg aag atc ata ctg ctc agg tac ttc aac cct gtt ggt gct cat      694
Asp Trp Lys Ile Ile Leu Leu Arg Tyr Phe Asn Pro Val Gly Ala His
180                 185                 190 cca agc gga cac atc ggt gaa gac ccc tct gga atc cca aac aac ctg      742
Pro Ser Gly His Ile Gly Glu Asp Pro Ser Gly Ile Pro Asn Asn Leu
                200                 205                 210 atg ccc tat gtc cag caa gtt gcc gtt ggg agg agg cct cac ctc act      790
Met Pro Tyr Val Gln Gln Val Ala Val Gly Arg Arg Pro His Leu Thr
        215                 220                 225 gtc tat gga acc gac tac aac aca aag gat gga act ggg gtg cgc gat      838
Val Tyr Gly Thr Asp Tyr Asn Thr Lys Asp Gly Thr Gly Val Arg Asp
    230                 235                 240 tat atc cat gtt gtt gac ctg gcc gat ggg cac ata gca gcc ctg ggg      886
Tyr Ile His Val Val Asp Leu Ala Asp Gly His Ile Ala Ala Leu Gly
245                 250                 255
```

-continued

| | | | | | | | | | | | | | | | | |
|---|---|---|---|---|---|---|---|---|---|---|---|---|---|---|---|---|
| aag | ctc | tat | gaa | gac | tct | gac | aga | ata | ggg | tgt | gag | gta | tac | aac | ctg | 934 |
| Lys | Leu | Tyr | Glu | Asp | Ser | Asp | Arg | Ile | Gly | Cys | Glu | Val | Tyr | Asn | Leu | |
| 260 | | | | | 265 | | | | | 270 | | | | | 275 | |
| ggc | aca | gga | aag | ggg | act | tcg | gtg | ctg | gaa | atg | gtg | gct | gca | ttc | gag | 982 |
| Gly | Thr | Gly | Lys | Gly | Thr | Ser | Val | Leu | Glu | Met | Val | Ala | Ala | Phe | Glu | |
| | | | | 280 | | | | | 285 | | | | | 290 | | |
| aag | gtt | tct | ggc | aag | aaa | atc | cct | ctg | gtg | ctt | gct | ggg | cga | aga | cct | 1030 |
| Lys | Val | Ser | Gly | Lys | Lys | Ile | Pro | Leu | Val | Leu | Ala | Gly | Arg | Arg | Pro | |
| | | | 295 | | | | | 300 | | | | | 305 | | | |
| gga | gat | gca | gag | att | gtt | tat | gct | gca | act | gcc | aag | gcc | gag | aaa | gag | 1078 |
| Gly | Asp | Ala | Glu | Ile | Val | Tyr | Ala | Ala | Thr | Ala | Lys | Ala | Glu | Lys | Glu | |
| | | 310 | | | | | 315 | | | | | 320 | | | | |
| ctg | aaa | tgg | aag | gcc | aag | tac | ggg | att | gaa | gag | atg | tgc | aga | gac | cag | 1126 |
| Leu | Lys | Trp | Lys | Ala | Lys | Tyr | Gly | Ile | Glu | Glu | Met | Cys | Arg | Asp | Gln | |
| | 325 | | | | | 330 | | | | | 335 | | | | | |
| tgg | aac | tgg | gca | agc | aaa | aac | ccc | tac | ggg | tat | gct | gga | tca | ccc | gac | 1174 |
| Trp | Asn | Trp | Ala | Ser | Lys | Asn | Pro | Tyr | Gly | Tyr | Ala | Gly | Ser | Pro | Asp | |
| 340 | | | | 345 | | | | | 350 | | | | | 355 | | | aac agc agc tgactgaaag caaatgcatg ctatgcatga tagggagatc 1223
Asn Ser Ser gagcagcaga ccacttacca ctgctagtaa aagaagtcga gtctcagaat accaccgtac 1283 gtatgcttac taaatagtcc gaggacggac ggacggatga tccatgtgtg gggcctcgta 1343 ttctcatttg tatagaggga cggagtagga gatccccagt ccatccatc cggcttattg 1403 ttgctaccgt caatccatgt ttaagaaata accccctatg catgtatgct tatcgatcta 1463 ctgtactagc taattatata ggcatatgta tatttgttag attcttatac aaaaaaaaaa 1523 aaaaaaaaaa aaaaaaa 1540

<210> SEQ ID NO 9
<211> LENGTH: 358
<212> TYPE: PRT
<213> ORGANISM: Seashore Paspalum

<400> SEQUENCE: 9

Met Val Ser Ala Val Leu Arg Thr Ile Leu Val Thr Gly Gly Ala Gly
1               5                   10                  15

Tyr Ile Gly Ser His Thr Val Leu Leu Leu Gln Gln Gly Phe Arg
            20                  25                  30

Val Val Val Val Asp Asn Leu Asp Asn Ala Ser Asp Val Ala Leu Ala
                35                  40                  45

Arg Val Ala Gln Leu Ala Ala Ser Ser Asn Gly Gly Ala Ala Asn Leu
            50                  55                  60

Val Phe His Lys Val Asp Leu Arg Asp Arg His Ala Leu Glu Asp Ile
65                  70                  75                  80

Phe Ser Ser His Arg Phe Glu Ala Val Ile His Phe Ala Gly Leu Lys
                85                  90                  95

Ala Val Gly Glu Ser Val Gln Lys Pro Leu Leu Tyr Tyr Asp Asn Asn
            100                 105                 110

Leu Ile Gly Thr Ile Thr Leu Leu Glu Val Met Ala Ala His Gly Cys
        115                 120                 125

Lys Lys Leu Val Phe Ser Ser Ala Thr Val Tyr Gly Trp Pro Lys
    130                 135                 140

Glu Val Pro Cys Thr Glu Glu Phe Pro Leu Cys Ala Thr Asn Pro Tyr
145                 150                 155                 160

Gly Arg Thr Lys Leu Val Ile Glu Asp Ile Cys Arg Asp Val His Arg

```
                        165                 170                 175
Ser Asp Pro Asp Trp Lys Ile Ile Leu Leu Arg Tyr Phe Asn Pro Val
            180                 185                 190

Gly Ala His Pro Ser Gly His Ile Gly Glu Asp Pro Ser Gly Ile Pro
            195                 200                 205

Asn Asn Leu Met Pro Tyr Val Gln Gln Val Ala Val Gly Arg Arg Pro
            210                 215                 220

His Leu Thr Val Tyr Gly Thr Asp Tyr Asn Thr Lys Asp Gly Thr Gly
225                 230                 235                 240

Val Arg Asp Tyr Ile His Val Val Asp Leu Ala Asp Gly His Ile Ala
                245                 250                 255

Ala Leu Gly Lys Leu Tyr Glu Asp Ser Asp Arg Ile Gly Cys Glu Val
            260                 265                 270

Tyr Asn Leu Gly Thr Gly Lys Gly Thr Ser Val Leu Glu Met Val Ala
            275                 280                 285

Ala Phe Glu Lys Val Ser Gly Lys Lys Ile Pro Leu Val Leu Ala Gly
            290                 295                 300

Arg Arg Pro Gly Asp Ala Glu Ile Val Tyr Ala Ala Thr Ala Lys Ala
305                 310                 315                 320

Glu Lys Glu Leu Lys Trp Lys Ala Lys Tyr Gly Ile Glu Glu Met Cys
            325                 330                 335

Arg Asp Gln Trp Asn Trp Ala Ser Lys Asn Pro Tyr Gly Tyr Ala Gly
            340                 345                 350

Ser Pro Asp Asn Ser Ser
            355

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
acagagccgc aaaaccacac                                            20

<210> SEQ ID NO 11
<211> LENGTH: 27
<212> TYPE: DNA
<213> ORGANISM: Artificial Sequence
<220> FEATURE:
<223> OTHER INFORMATION: Synthetic DNA

<400> SEQUENCE: 11
ttcgtagcta ggcacattcg agcggtg                                    27

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
gtcgtcgaca acttccacaa                                            20

<210> SEQ ID NO 13
<211> LENGTH: 20
<212> TYPE: DNA
<213> ORGANISM: Artificial Sequence
```

```
<220> FEATURE:
<223> OTHER INFORMATION: Synthetic DNA

<400> SEQUENCE: 13
ttgttctcgt agtacatgtc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
atgaaaaagc ctgaactcac                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
cgaacccgct cgtctggcta                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
gtggtcgaca acttccacaa                                              20

<210> SEQ ID NO 17
<211> LENGTH: 17
<212> TYPE: DNA
<213> ORGANISM: Artificial Sequence
<220> FEATURE:
<223> OTHER INFORMATION: Synthetic DNA

<400> SEQUENCE: 17
ttgttctcgt acatgta                                                 17
```

GENE CAPABLE OF IMPARTING SALT STRESS RESISTANCE

TECHNICAL FIELD

The present invention relates to a gene that imparts salt stress tolerance and a transgenic plant into which such gene has been introduced.

BACKGROUND ART

Plants receive environmental stresses, such as salt, dehydration, high temperature, low temperature, intense light, air pollution, and the like. Salt damage and dehydration are the most problematic stresses from the viewpoint of agricultural production. Salt damage occurs not only in areas that originally have a high salt content but also in farmland due to irrigation, which was problem-free in the past. At present, agricultural lands over as large an area as 12,000,000 hectares suffer damage due to salt or drought in Asia, and agricultural lands over as large an area as 9,500,000 hectares actually remain unused due to salt damage. In particular, rice is a staple grain in Asia. If salt stress tolerance could be imparted to rice, accordingly, unused farmland could be converted for food production. This would positively affect the stabilization of grain production in the world. Up to the present, a variety of attempts have been made in order to produce environmental stress tolerant plants that can be cultivated under bad environmental conditions or in poor soil via gene recombinant technologies. For example, a gene, the expression of which is induced by salt stress, may be isolated and then allowed to express, thereby producing salt tolerant plants. Examples of known genes that impart salt stress tolerance include the betaine synthase gene derived from manila grass (*Zoysia matrella*) (JP Patent Publication (Unexamined) No. 2001-309789), the choline oxidase gene derived from *Arthrobacter globiformis* (Mohanty A., et al., Theor. Appl. Genet., 106, pp. 51-57, 2002), the chloroplast glutamine synthase derived from rice (Hoshida H., et al., Plant Mol. Biol. 43, pp. 103-111, 2000), the active transcription factor derived from rice (OSDREB; Dobouzet J. G., et al., Plant J. 33, pp. 751-763, 2003), and the Na+/H+ antiporter gene derived from *Atriplex gmelinii* var. *spontanea* (JP Patent Publication (Unexamined) No. 2000-157287). Among the enzyme genes associated with sugar metabolism or synthesis, the genes associated with trehalose synthesis derived from *E. coli* (Jang I. C., et al., Plant Physiol., 131, pp. 516-524, 2003) and the galactinol synthase (AtGloS) genes that synthesize galactinol from UDP galactose have been reported to be associated with impartation of water stress tolerance such as dehydration, salt, or low temperature stress to *Arabidopsis thaliana* ("Saibou Kougaku (Cell Technology)," vol. 21, No. 12, pp. 1455-1459, 2002; Teruaki T. et al., The Plant Journal, 29 (4), pp. 417-426, 2002). In the case of dicotyledonous plants, there has been an example wherein the salt stress tolerance of plants has been evaluated with a salt concentration of 200 mM over a period of 10 weeks in tomatoes transformed with the Na+/H+ antiporter genes derived from *Arabidopsis thaliana* (Zhang H. X., Blumwald E., Nature Biotechnol., 19, pp. 765-768, 2001) or in *Brassica* plants (Zhang H. X. et al., Proc. Natl. Acad. Sci. U.S.A., 98, pp. 12832-12836, 2001), and harvests of fruits or seeds have been reported. In the case of monocotyledonous transgenic plants, however, there has been no gene that imparted salt stress for a long period of time from transplantation to seed harvesting. For example, transgenic rice exhibits salt stress tolerance for only a short period of time of 13 days at 100 mM, 2 weeks at 150 mM, and 3 days at 300 mM. Accordingly, it is difficult to consider that the aforementioned genes could impart salt tolerance to plants that would be efficient for the actual process of production over a period of from several weeks to several months, from seedling transplantation to seed harvesting, under the present circumstances.

UDP-glucose 4-epimerase is an enzyme that catalyzes bilateral reactions from UDP glucose to UDP galactose and vice versa. Up to the present, the plant-derived UDP-glucose 4-epimerase gene (hereafter it may be referred to as the "UGE gene") has been isolated from, for example, *Arabidopsis thaliana* or guar (Reiter W. D., Vanzin G. F., Plant Mol. Biol., 47, pp. 95-113, 2001). However, there has been no UGE gene that is known to be capable of imparting salt stress tolerance. Also, no plant species wherein the expression of UGE genes is induced by salt stress has been reported.

Galactose inhibits growth at the shoot in the process of gemmation of the dicotyledonous plant *Arabidopsis thaliana*. This is considered to result from accumulation of UDP-galactose or galactose-1-phosphoric acid because the plant could not use up externally provided galactose. In the case of plants into which the 35S and nosT expression cassettes of the UGE genes of *Arabidopsis thaliana* have been introduced, it is reported that growth is unlikely to be inhibited even in the presence of galactose. Also, the availability of the UGE gene as a selection marker for a transgenic plant has been pointed out (Reiter W. D., Vanzin G. F., Plant Mol. Biol., 47, pp. 95-113, 2001; Dormann P. and Benning, C., the Plant Journal, 13, pp. 641-652, 1998). It is considered that the growth of the plants into which UGE genes have been introduced is not inhibited in the presence of galactose, because the UGE genes convert the accumulated UDP-galactose to UDP-glucose. In contrast, it is reported that galactose has the effect of inhibiting the stretching growth of some tissues of seedlings, coleoptiles or sheath leaves, and seminal roots by phytohormones, such as auxin or gibberellin, of monocotyledonous plants (Inouhe M., et al., Physiologia Plantalum, 66, pp. 370-376, 1986); however, there has been no report or research on the influence thereof on physiological phenomena associated with tissue culturing, such as rooting. There have been no reports of any experiments, whereby the growth of monocotyledonous plants, including grass, in the presence of galactose is inspected by introducing the UGE genes therein.

Further, antibiotic tolerant genes, such as kanamycin tolerant genes or hygromycin tolerant genes, remain in genetically engineered organisms (GMO). This is the most serious issue of concern in recent years, in terms of the safety of GMO. Such genes are referred to as selection markers (marker genes) for screening the cells into which the target genes have been effectively introduced at an early stage. They become unnecessary after regeneration of plants from cells, rooting, and acclimation. In contrast, a method of selection that involves the use of sugar, which is considered to impose a slighter influence on human bodies, has been reported in recent years. In this method, the sugar isomerase genes of microorganisms are employed as markers, and selection can be made with the use of xylose (Haaldrup A., et al., Plant Cell Reports, 18, pp. 76-81, 1998) or mannose (Joersbo M., et al., Molecular Breeding, 4, pp. 111-117, 1998). These marker genes are, however, derived from microorganisms, and the safety of their DNA cannot be perfectly ensured, since humans have not ever ingested such DNA as food. Therefore, the development of highly safe selection markers that can serve as alternatives to antibiotic tolerant genes and expression vectors using the same has been awaited.

Accordingly, an object of the present invention is to provide a novel gene that can impart salt stress tolerance to plants for a long period of time and salt stress-tolerant transgenic plants into which such gene has been introduced. It is another object of the present invention to provide highly safe selection markers that can serve as alternatives to antibiotic tolerant genes.

DISCLOSURE OF THE INVENTION

The present inventors have conducted concentrated studies in order to attain the above objects. They focused on the fact that seashore paspalum has a gene of which expression is induced by salt stress, and attempted to clone the same. As a result, they discovered that the aforementioned gene encodes UDP-glucose 4-epimerase. This has led to the completion of the present invention.

Specifically, the present invention includes the following.

(1) A gene encoding the following protein (a), (b), or (c):

(a) a protein consisting of the amino acid sequence as shown in SEQ ID NO: 2 in the Sequence Listing;

(b) a protein consisting of an amino acid sequence derived from the amino acid sequence as shown in SEQ ID NO: 2 in the Sequence Listing by deletion, substitution, or addition of one or several amino acid residues and having activity of imparting salt stress tolerance to plants; or (c) a protein consisting of an amino acid sequence derived from the amino acid sequence as shown in SEQ ID NO: 2 in the Sequence Listing by deletion, substitution, or addition of one or several amino acid residues and having UDP-glucose 4-epimerase activity.

(2) A gene consisting of the following DNA (d), (e), or (f):

(d) DNA consisting of the nucleotide sequence as shown in SEQ ID NO: 1 in the Sequence Listing;

(e) DNA hybridizing under stringent conditions to DNA consisting of a nucleotide sequence complementary to DNA consisting of the nucleotide sequence as shown in SEQ ID NO: 1 in the Sequence Listing and encoding a protein having activity of imparting salt stress tolerance to plants; or (f) DNA hybridizing under stringent conditions to DNA consisting of a nucleotide sequence complementary to DNA consisting of the nucleotide sequence as shown in SEQ ID NO: 1 in the Sequence Listing and encoding a protein having UDP-glucose 4-epimerase activity.

(3) A recombinant vector comprising the gene according to (1) or (2).

(4) A transgenic plant into which the gene according to (1) or (2) or the recombinant vector according to (3) has been introduced.

(5) A salt stress tolerant transgenic plant into which the gene according to (1) or (2) or the recombinant vector according to (3) has been introduced.

(6) The transgenic plant according to (4) or (5), wherein the plant is monocotyledonous.

(7) The transgenic plant according to (6), wherein the monocotyledonous plant belongs to the family Gramineae, Liliaceae, or Zingiberaceae.

(8) The transgenic plant according to (7), wherein the plant that belongs to the family Gramineae is selected from the group consisting of rice, barley, wheat, maize, sugarcane, Zoysia, sorghum, Italian millet, and Japanese millet.

(9) The transgenic plant according to (4) or (5), wherein the plant is dicotyledonous.

(10) The transgenic plant according to (9), wherein the dicotyledonous plant belongs to the family Brassicaceae, Solanaceae, Leguniinosae, Cucurbitaceae, Umbelliferae, Asteraceae, Malvaceae, Chenopodiaceae, Myrtaceae, or Salicaceae.

(11) A method for imparting salt stress tolerance to plants, wherein the gene according to (1) or (2) or the recombinant vector according to (3) is introduced into plants.

(12) A selection marker for a transgenic plant comprising the gene according to (1) or (2).

(13) The selection marker for a transgenic plant according to (12), wherein the plant is monocotyledonous.

(14) The selection marker for a transgenic plant according to (13), wherein the monocotyledonous plant belongs to the family Gramineae, Liliaceae, or Zingiberaceae.

(15) The selection marker for a transgenic plant according to (14), wherein the plant that belongs to the family Gramineae is selected from the group consisting of rice, barley, wheat, maize, sugarcane, Zoysia, sorghum, Italian millet, and Japanese millet.

(16) The selection marker for a transgenic plant according to (12), wherein the plant is dicotyledonous.

(17) The selection marker for a transgenic plant according to (16), wherein the dicotyledonous plant belongs to the family Brassicaceae, Solanaceae, Leguminosae, Cucurbitaceae, Unibelliferae, Asteraceae, Malvaceae, Chenopodiaceae, Myrtaceae, or Salicaceae.

(18) A method for selecting a transgenic plant comprising introducing the gene according to (1) or (2) or the recombinant vector according to (3) into a plant, culturing the plant in galactose-containing medium, and selecting the transgenic plant by employing galactose tolerance as an indicator.

BRIEF DESCRIPTION OF THE DRAWINGS

FIG. 2A shows the results of Northern analysis using a Ps ABA probe, and FIG. 2B shows the results of Northern analysis using a Ps UGE probe.

FIG. 4 shows the amino acid comparison of the UGE homolog belonging to group No. 1 classified by the phylogenetic tree, Ps UGE1 (SEQ ID NO: 2), and Ps UGE2 (SEQ ID NO: 9), with AT1g12780 (SEQ ID NO: 18), At1g63180, (SEQ ID NO: 19), and Ct UGE (SEQ ID NO: 20).

FIG. 7 shows the results of detecting the Ps UGE genes in the T0 generation of the Ps UGE transgenic Nipponbare and the F1 generation resulting from the crossing of the T0 generation of Nipponbare and Koshihikari via genomic PCR (upper portion: T0 generation of Nipponbare, lower portion: F1 generation resulting from the crossing of the T0 generation of Nipponbare and Koshihikari). An arrow points to the position of a band corresponding to a 226-bp internal sequence of the Ps UGE gene, V indicates a PCR product obtained when the expression vector Ps UGE1a/pBI221 is used as a template, and NT indicates a genomic PCR product of a non-transgenic rice plant. The upper portion of FIG. 7 shows that bands indicating the presence of the Ps UGE gene were observed in 20 out of the 22 individuals of the T0 generation of hygromycin tolerant plants. The lower portion (left and right sides)

of FIG. 7 shows that of the F1 generation resulting from the crossing of the T0 generation of Nipponbare plants and non-transgenic Koshihikari, the presence of the Ps UGE gene was observed in the genomes of 29 out of the 46 individuals.

Figure 8:
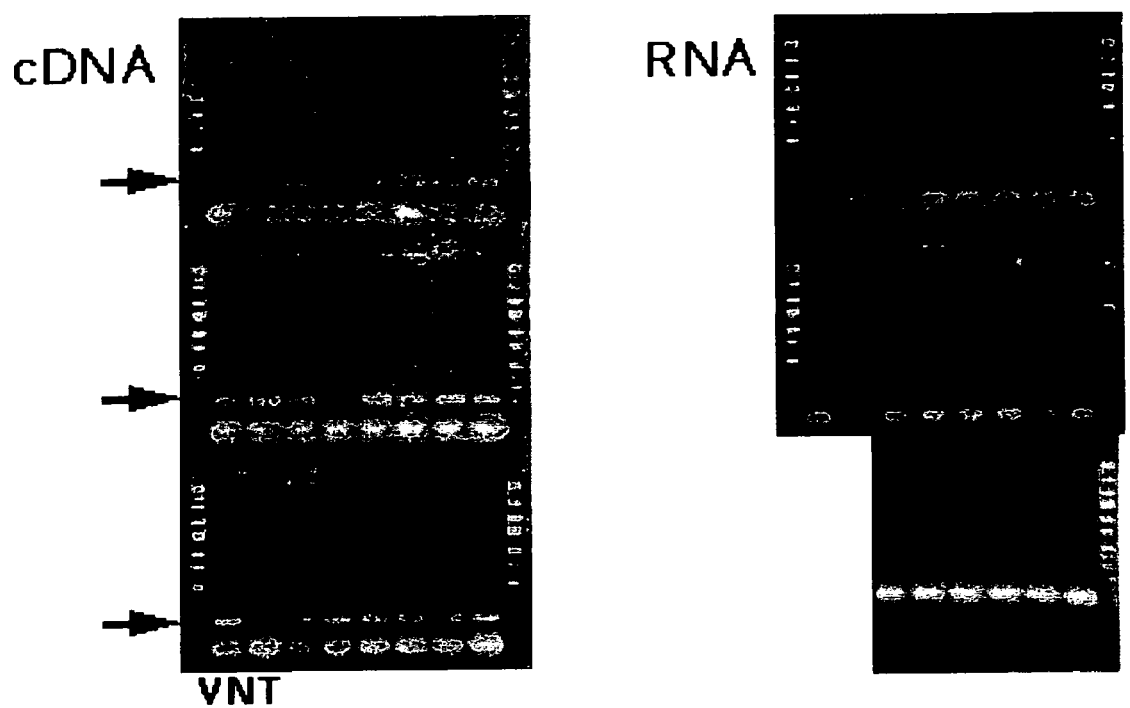

FIG. 8 shows the confirmation of Ps UGE gene expression in the T0 generation of Nipponbare via RT-PCR. An arrow points to the position of a band corresponding to a 226-bp internal sequence of the Ps UGE gene, V indicates a PCR product obtained when the expression vector Ps UGE1a/pBI221 is used as a template, and NT indicates an RT-PCR product when the first strand cDNA of a non-transgenic rice plant is used as a template. The left portion of FIG. 8 shows bands indicating the transcription of the Ps UGE gene were observed in 20 out of the 22 individuals of the T0 generation of hygromycin tolerant plants, when cDNA was used as a template. In contrast, no band was observed regarding the total RNA used for the synthesis of the first strand cDNA (right portion of FIG. 8).

Figure 9:
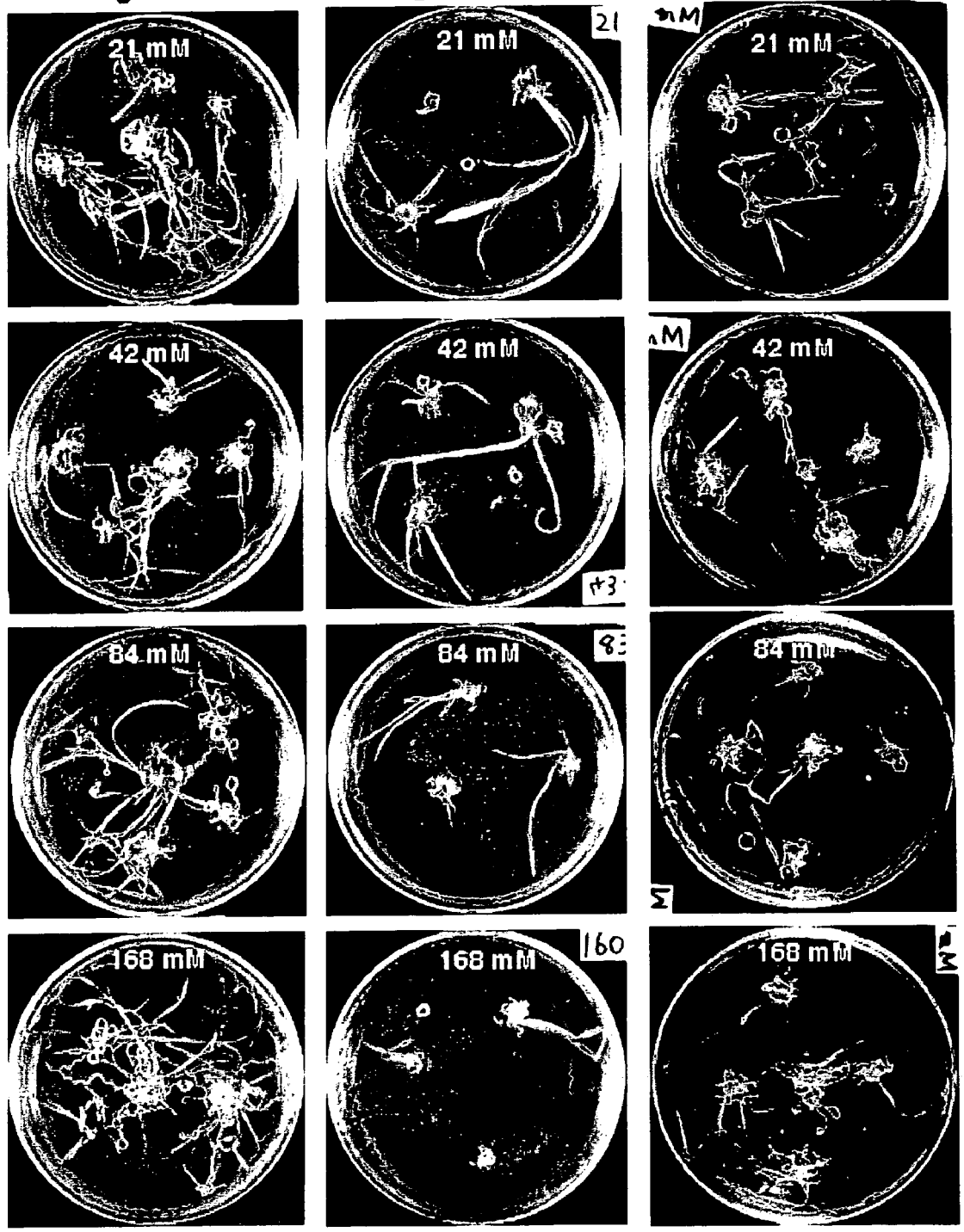

FIG. 9 shows a photograph of rooting of the Ps UGE transgenic rice (35S:Ps UGE1a:nosT) and of a plant redifferentiated from the callus of a non-transgenic rice plant (the control), when they are allowed to grow in media containing galactose at various levels.

Figure 10:
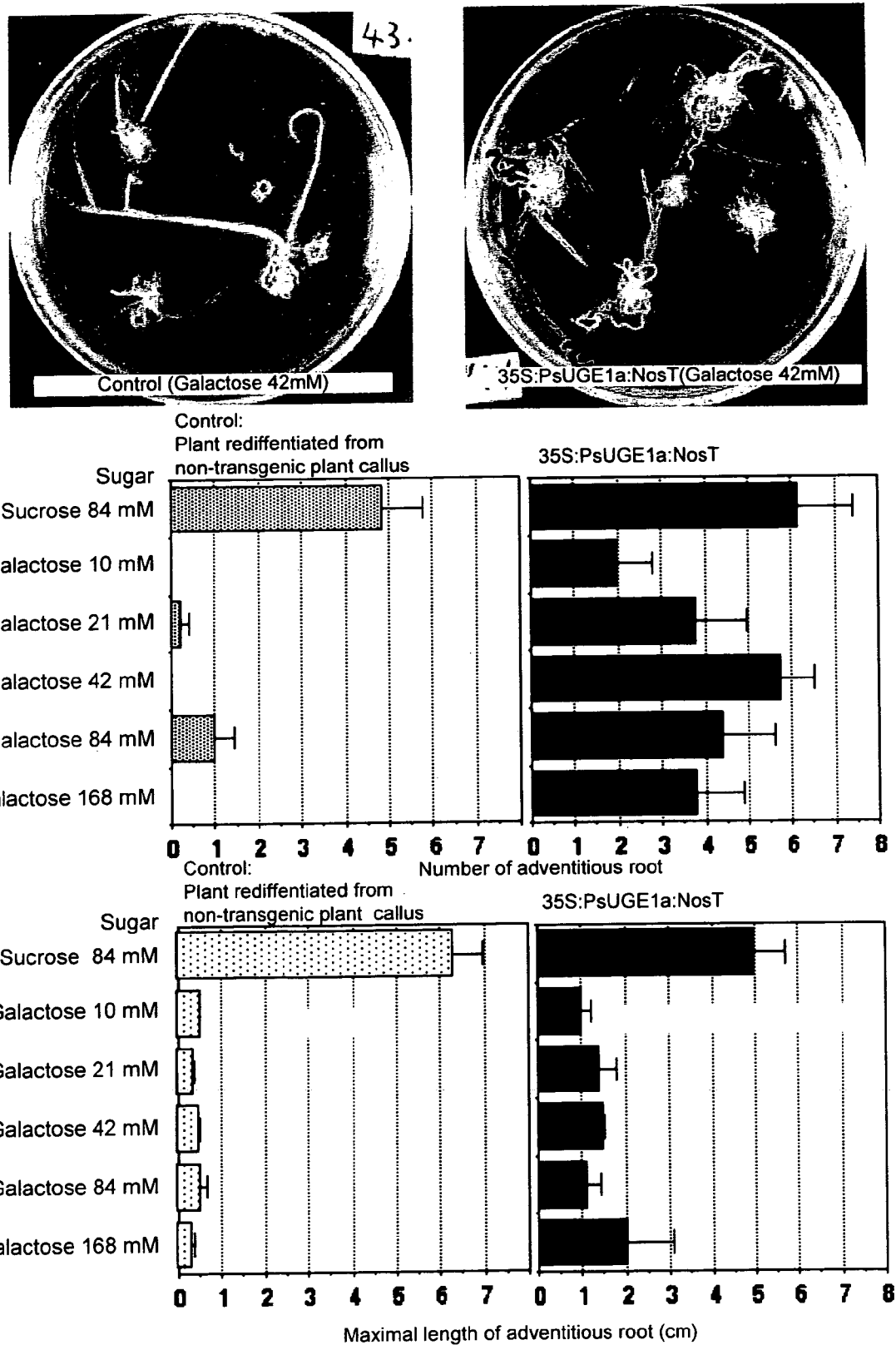

FIG. 10 shows a photograph of rooting of the Ps UGE transgenic rice (35S:Ps UGE1a:nosT; upper right) and that of a plant redifferentiated from the callus of a non-transgenic rice plant (the control; upper left), when they are allowed to grow in a medium containing galactose. The middle section of FIG. 10 shows the number of adventitious roots, while the bottom section of FIG. 10 shows the maximal length of adventitious roots (cm).

FIG. 11 shows a photograph of the shoots of the Ps UGE transgenic rice (35S:Ps UGE1a:nosT; upper right) and that of a plant redifferentiated from the callus of a non-transgenic rice plant (the control; upper left), when they are allowed to grow in a medium containing galactose. The middle section of FIG. 11 shows the maximal length of the shoot (cm) for the control, while the bottom section of FIG. 11 shows the maximal length of the shoot (cm) for 35S:Ps UGE1a:nosT.

Figure 12:
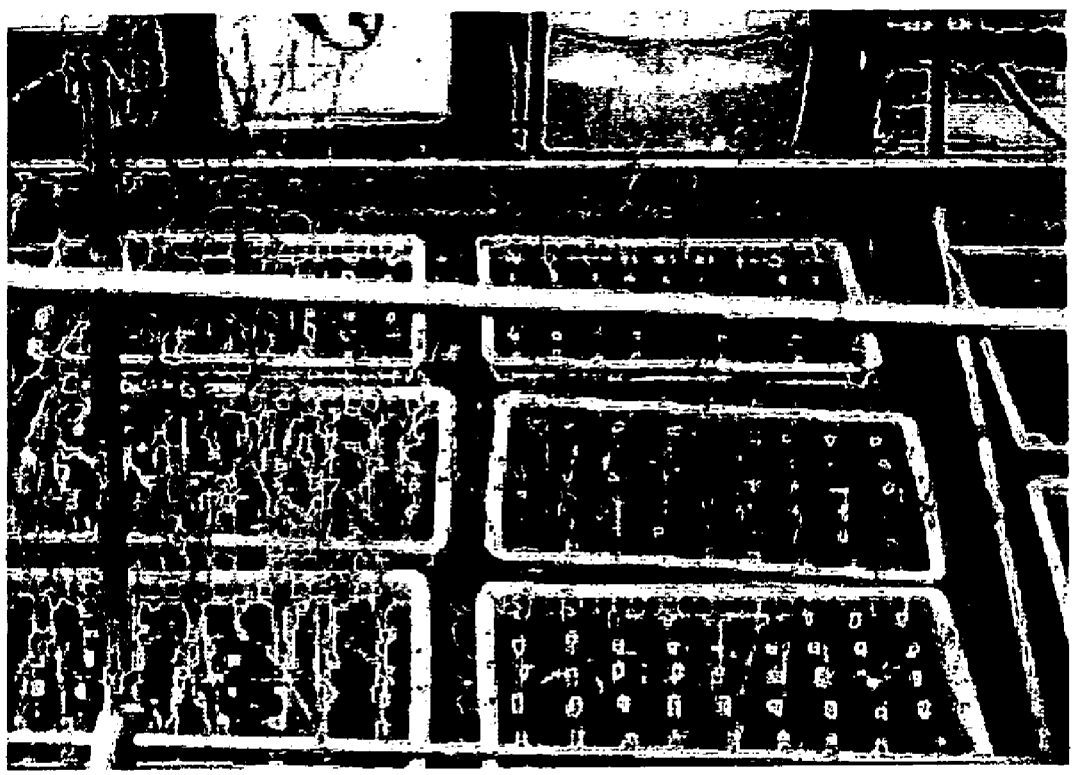

FIG. 12 shows the progress of the test for evaluating the salt stress (NaCl, 3,000 ppm) tolerance of the T0 generation of the Ps UGE transgenic Nipponbare.

Figure 13:
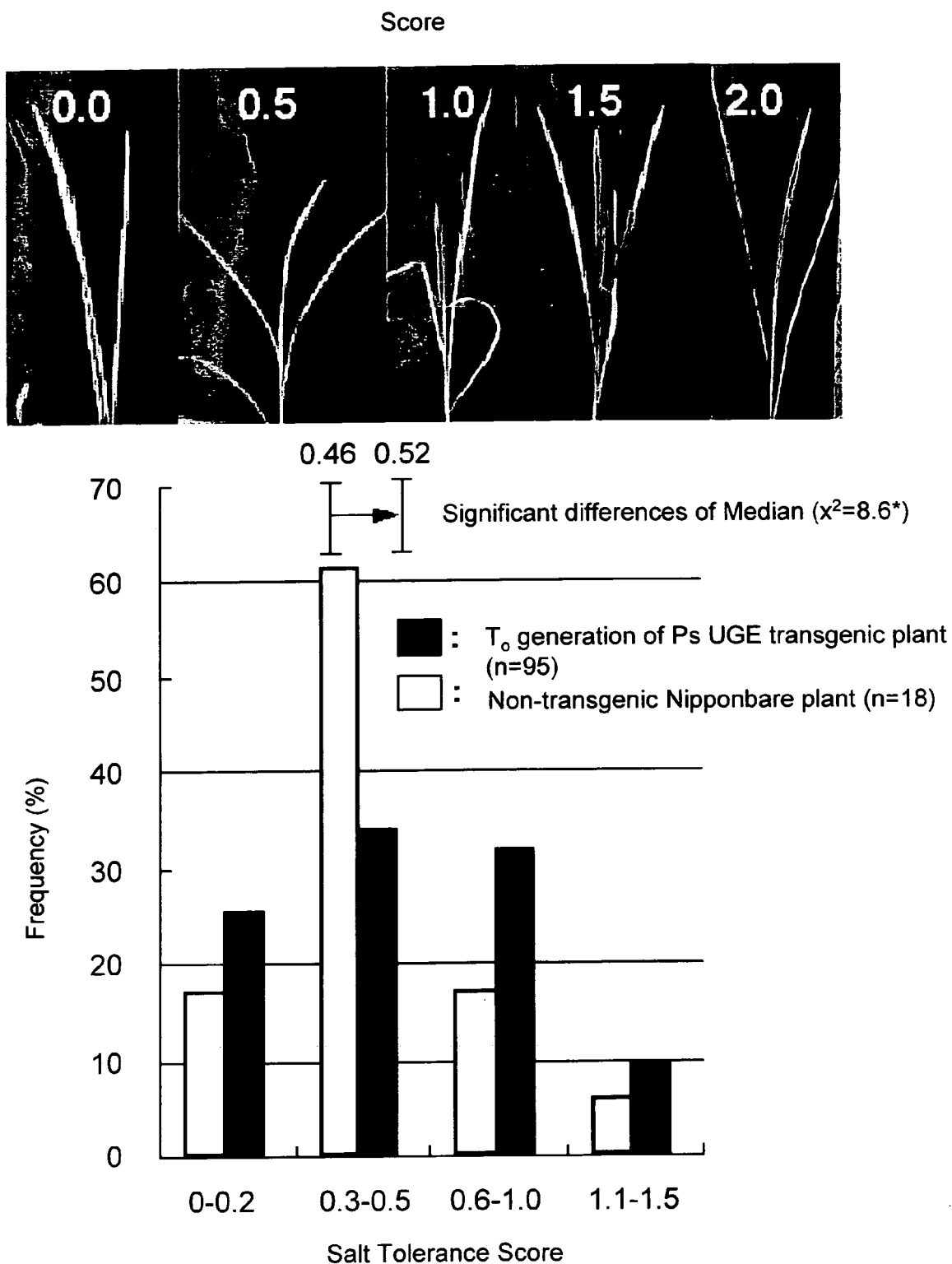

FIG. 13 shows the results of the test for evaluating the salt stress (NaCl, 3,000 ppm) tolerance of the T0 generation of the Ps UGE transgenic Nipponbare. The degree of leaf blight was visually inspected in the 10th week, and each plant was scored in accordance with the definitions of scores according to the method of IRRI (Table 2). The upper portion of FIG. 13 illustrates the plant at each "score". The lower portion of FIG. 13 shows the observed frequency of each salt tolerance score.

FIG. 14 shows the results of the test for evaluating the salt stress (NaCl, 3,000 ppm) tolerance of the F1 generation (resulting from the crossing of the T0 generation of Nipponbare and Koshihikari) of the Ps UGE transgenic rice.

Figure 15:

FIG. 15 shows the conditions of ear emergence of the Ps UGE transgenic rice (F1 generation) after being cultured for 6 weeks under salt stress application.

Figure 16:
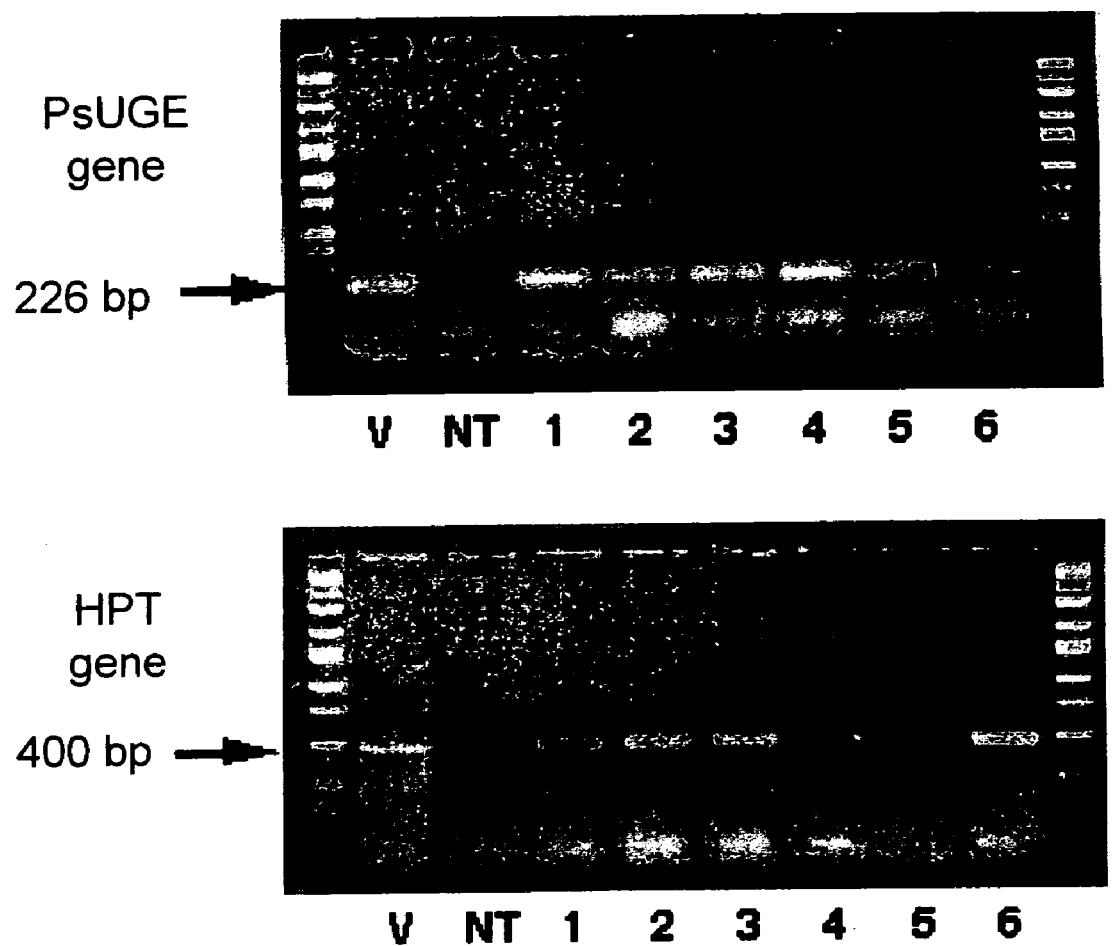

FIG. 16 shows the results of genomic PCR on plants selected with galactose (upper portion: the Ps UGE gene; lower portion: the hygromycin tolerant gene). The 6 plants (lanes 1-6 in the upper and lower portions of FIG. 16) in Example 7 were subjected to genomic PCR to confirm the gene introduction using the sense primer (SEQ ID NO: 14) and the antisense primer (SEQ ID NO: 15) of the hygromycin resistant (HPT) gene that is introduced simultaneously with the Ps UGE gene with the internal sequence primers (SEQ ID NOs: 12 and 13) and the expression vector Ps UGE1a/pBI221Hm of the Ps UGE gene that had been introduced. In the upper portion the presence of the 226-bp band of the Ps UGE gene was assessed and in the lower portion the presence of the 400-bp band of the internal sequence of the hygromycin resistant (HPT) gene was assessed.

Figure 17:

FIG. 17 shows the results of detecting the Ps UGE gene in the Ps UGE transgenic *Arabidopsis thaliana* via genomic Southern hybridization (lane 1: non-transgenic plants; lanes 2 to 5: Ps UGE transgenic plants).

Figure 18:
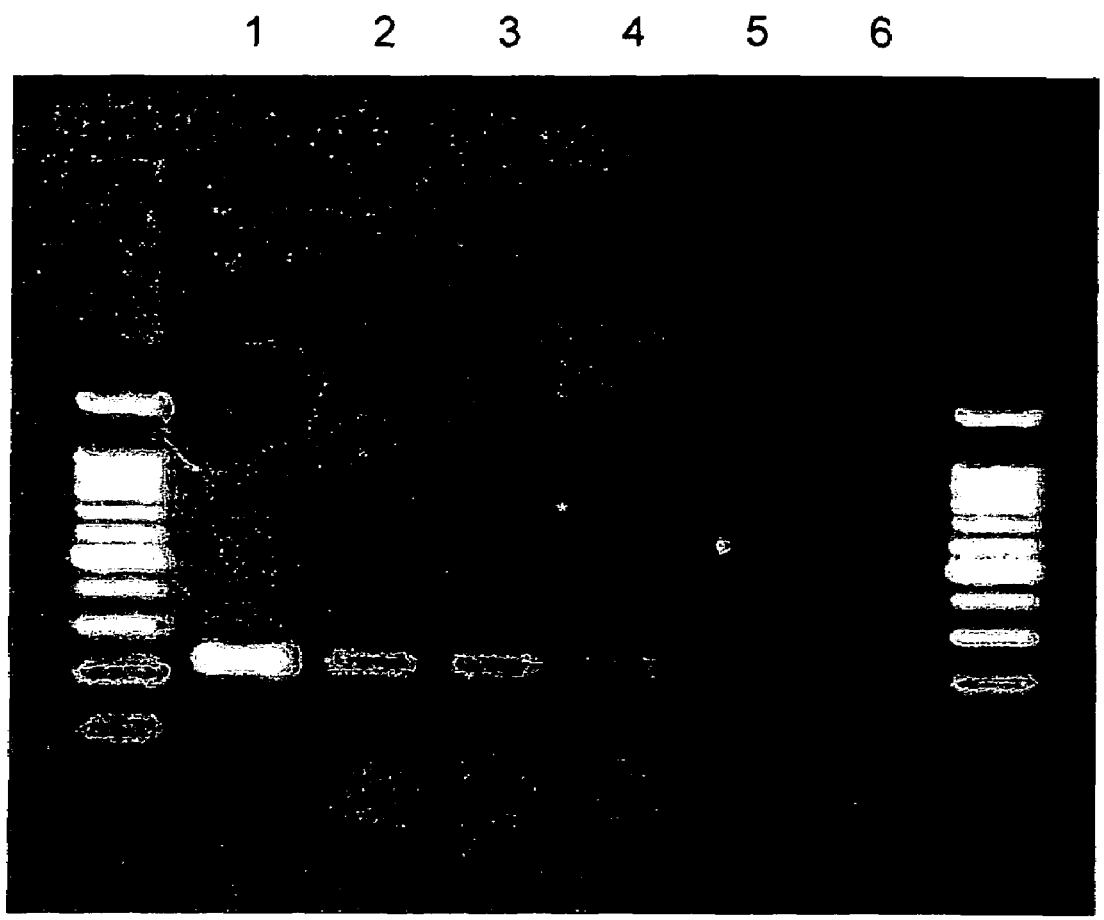

FIG. 18 shows the results of confirming Ps UGE gene expression in the Ps UGE transgenic *Arabidopsis thaliana* via RT-PCR (lane 1: the vector (pBI122); lane 2: the Ps UGE transgenic plant (Ps 6-3); lane 3: the Ps UGE transgenic plant (Ps 10-1); lane 4: the Ps UGE transgenic plant (Ps 15-5); lane 5: without template; lane 6: without primers).

Figure 19:
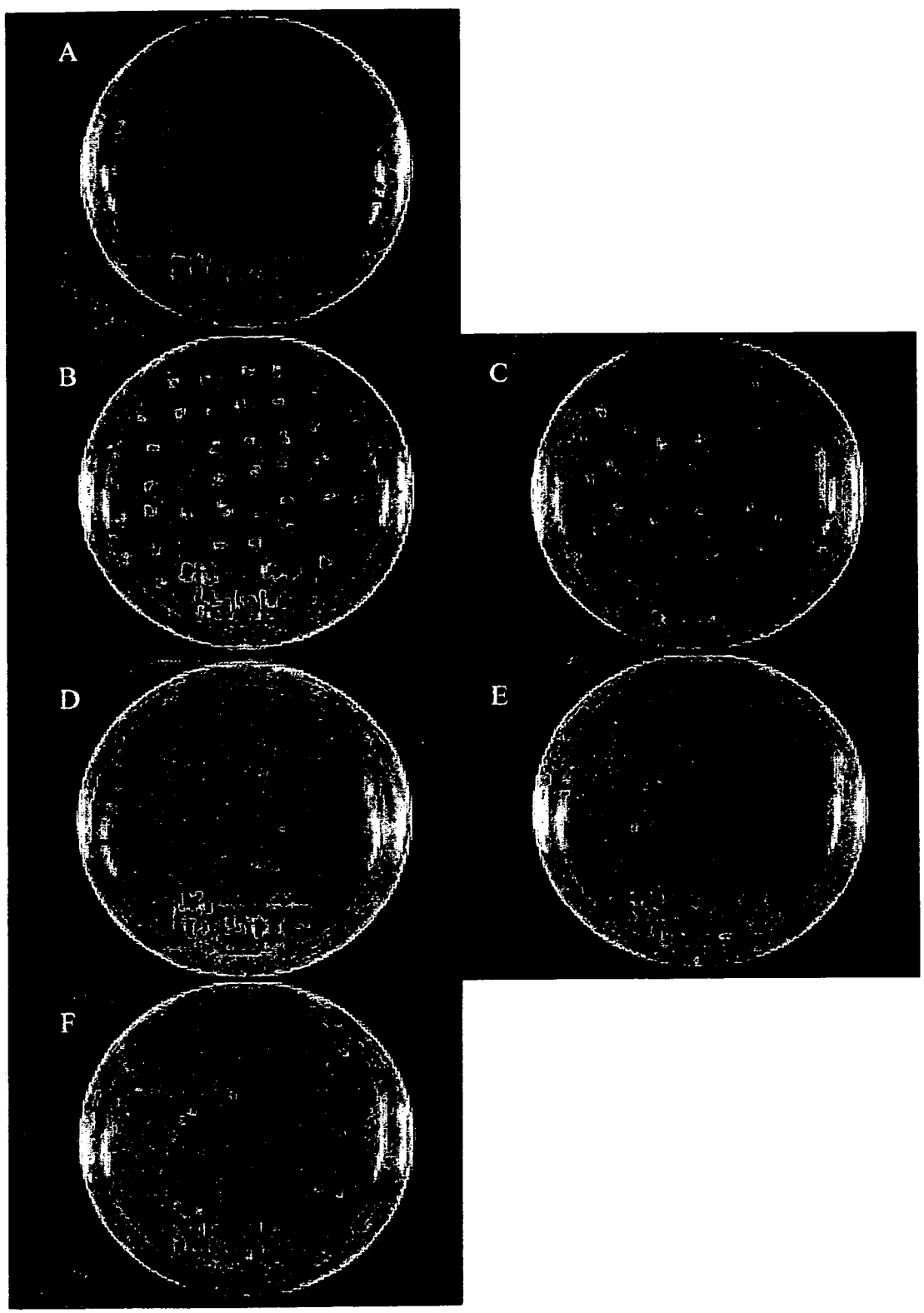

FIG. 19 shows a photograph of the Ps UGE transgenic *Arabidopsis thaliana* plants grown in media containing galactose (medium A containing sucrose) (A: a non-transgenic plant; B: a non-transgenic plant; C: a vector (pBI122); D: the Ps UGE transgenic plant (Ps 6-3); E: the Ps UGE transgenic plant (Ps 11-1); F: the Ps UGE transgenic plant (Ps 15-5)).

Figure 20:
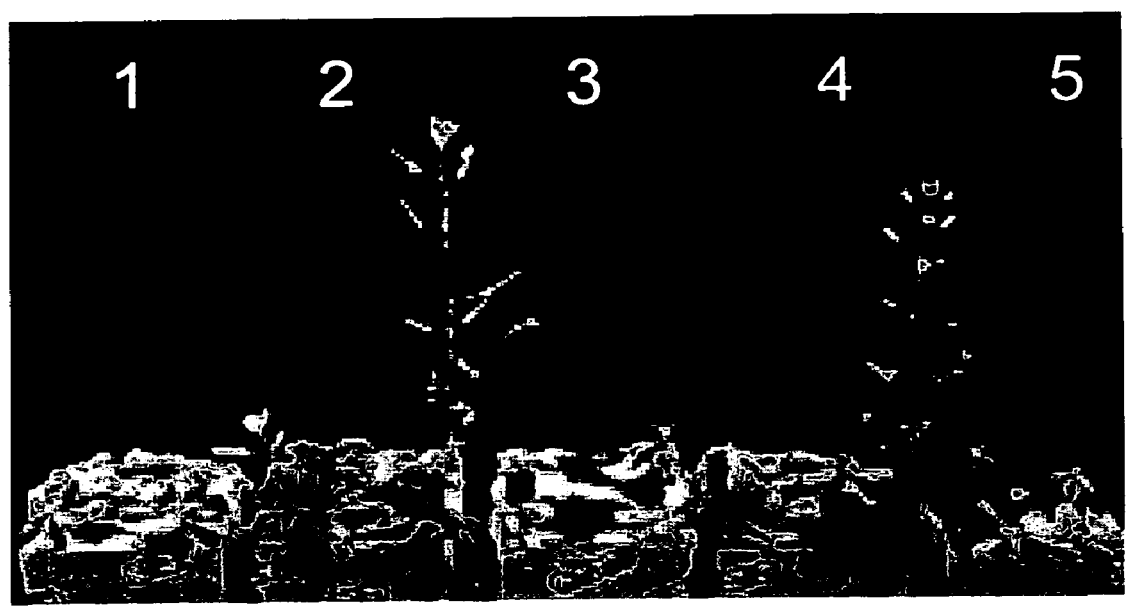

FIG. 20 shows the growth conditions of the Ps UGE transgenic *Arabidopsis thaliana* plants that had been cultured for 7 days under salt stress application (1: a non-transgenic plant, 2: the Ps UGE transgenic plant (Ps 6-3), 3: the Ps UGE transgenic plant (Ps 10-1), 4: the Ps UGE transgenic plant (Ps 11-1), 5: the Ps UGE transgenic plant (Ps 15-5)).

Hereafter, the present invention is described in detail. This patent application claims priority from Japanese Patent Application No. 2003-113194 filed on Apr. 17, 2003, and Japanese Patent Application No. 2004-075932 filed on Mar. 17, 2004, and includes part or all of the contents as disclosed in the descriptions and/or drawings thereof.

1. Gene Cloning (1) Preparation and Screening of cDNA Library

The gene that imparts salt stress tolerance according to the present invention can be obtained, for example, in the following manner. At the outset, seashore paspalum is cultivated while seawater or salt stress is applied (the salt stress group) and seawater or salt stress is not applied (the control group). Total RNA is prepared therefrom, and PCR is carried out using the single-stranded cDNA prepared with the use of oligo dT as a template to prepare a salt stress probe and a control probe.

Subsequently, these two types of probes (a salt stress probe and a control probe) are used to select clones that are detected specifically with the use of the salt stress probe from the seashore paspalum cDNA library via differential screening. Northern analysis is then carried out using the probe prepared from the partial sequence of cDNA contained in the clones. Secondary selection of clones, the expression of which is induced by salt stress in seashore paspalum but is not induced in rice, is carried out. Finally, the selected clones are used as probes to obtain clones containing the target gene from the cDNA library prepared from seashore paspalum to which salt stress has been applied.

mRNA can be extracted from seashore paspalum (described in, for example, Duedck A. E. and Peacock C. H., Agronomy Journal, vol. 77, pp. 47-50, 1985), and the cDNA library thereof can be prepared in accordance with conventional techniques. An example of an mRNA source is a mature leaf of seashore paspalum, although such sources are not limited thereto. mRNA can be prepared in accordance with a conventional technique. For example, total RNA is extracted from the aforementioned source via the guanidium thiocyanate-cesium trifluoroacetate method, and poly(A)+RNA (mRNA) can be then obtained via an affinity column method using oligo(dt) cellulose or poly(U) Sepharose or the batch method. Further, poly(A)+RNA may be fractionated via, for example, sucrose density gradient centrifugation.

Subsequently, single-stranded cDNA is synthesized using the obtained mRNA as a template, oligo(dT) primers, and reverse transcriptase, and double-stranded cDNA is then synthesized from the single-stranded cDNA using DNA synthase I, DNA ligase, Rnase H, or the like. The synthesized double-stranded cDNA is blunt-ended with T4 DNA synthase, an adaptor (e.g., EcoRI adaptor) is ligated thereto, phosphoryration is carried out, and the resulting cDNA is packaged in vitro into the λgt11 or another vector. Thus, a cDNA library can be prepared. In addition to λ phages, plasmids can be used to prepare such a cDNA library.

When λ phages (e.g., λgt11) are used, for example, PCR using primers for λgt11 insert amplification can be adopted in order to select a clone having DNA of interest from among the transformants thus obtained.

An example of template DNA used herein is cDNA synthesized from the aforementioned mRNA via reverse transcription. Commercially available random hexamers and the like can be used as primers.

Extraction of mRNA, preparation of the cDNA library, preparation of probes, and differential screening of the cDNA library are described in detail in Example 1. Expression of the cloned genes is induced by salt stress application in paspalum, and this can be confirmed via Northern blot analysis, RT-PCR, or other means, which are techniques of gene expression analysis. Such confirmation is described in detail in Example 3.

(2) Determination of Nucleotide Sequence

The nucleotide sequence of the cDNA of the obtained clone of interest is determined using the PCR product as a template. The nucleotide sequence can be determined via conventional techniques such as the chemical modification technique of Maxam-Gilbert or the dideoxynucleotide chain termination method utilizing the M13 phage. In general, sequencing is carried out using an automated nucleotide sequencer (e.g., the ABI373 Sequencer and the 310 DNA Sequencer, Applied Biosystems). The determined nucleotide sequence is analyzed using DNA analyzing software such as DNASIS (Hitachi Software Engineering Co., Ltd), and a protein-encoding region that is encoded in the obtained DNA strand can be found.

The gene that imparts salt stress tolerance according to the present invention (hereafter it may be referred to as the "Ps UGE gene") encodes the protein consisting of the amino acid sequence as shown in SEQ ID NO: 2.

The gene according to the present invention includes a gene encoding a protein consisting of an amino acid sequence derived from the amino acid sequence as shown in SEQ ID NO: 2 by deletion, substitution, or addition of one or several amino acid residues and having activity of imparting salt stress tolerance to plants.

Further, the gene according to the present invention includes a gene encoding a protein consisting of an amino acid sequence derived from the amino acid sequence as shown in SEQ ID NO: 2 by deletion, substitution, or addition of one or several amino acid residues and having UDP-glucose 4-epimerase activity.

The number of the amino acid residues that may be deleted, substituted, or added is preferably 1 to several. For example, 1 to 10, and preferably 1 to 5, amino acid residues may be deleted from the amino acid sequence as shown in SEQ ID NO: 2; 1 to 10, and preferably 1 to 5, amino acid residues may be added to the amino acid sequence as shown in SEQ ID NO: 2; or 1 to 10, and preferably 1 to 5, amino acid residues may be substituted with other amino acid residues in the amino acid sequence as shown in SEQ ID NO: 2.

The gene according to the present invention includes a gene encoding a protein consisting of an amino acid sequence having 65% or higher homology to the amino acid sequence as shown in SEQ ID NO: 2 and having activity of imparting salt stress tolerance to plants.

Further, the gene according to the present invention includes a gene encoding a protein consisting of an amino acid sequence having 65% or higher homology to the amino acid sequence as shown in SEQ ID NO: 2 and having UDP-glucose 4-epimerase activity.

The aforementioned 65% or higher homology preferably refers to homology of 75% or higher, more preferably to homology of 85% or higher, and most preferably to homology of 95% or higher.

The term "activity of imparting salt stress tolerance to plants" used herein refers to the activity of imparting to plants resistance to salt stress. Such activity can be evaluated by continuously subjecting the plants to salt stress of 0.3% to 3.0% NaCl for 2 to 8 weeks and then observing the growth conditions thereof in terms of, for example, visual inspection, survival, yield, and amount of growth. The results of visual inspection of the rice growth conditions can be quantified using salt tolerance scores of the International Rice Research Institute (IRRI). The NaCl concentration of salt stress varies depending on the types of plants. For example, a NaCl concentration can be made to be 0.3% in the case of rice, 1% in the case of barley, and 0.3% to 1% in the case of wheat and maize.

When the numerical values obtained in any one, and preferably 2 or more, of the aforementioned terms are higher than those of control plants (e.g., non-transgenic plants), the plants can be evaluated as "having activity."

The term "activity of imparting salt stress tolerance to plants" is substantially the same as the activity of a protein that has the amino acid sequence as shown in SEQ ID NO: 2.

The term "UDP-glucose-4-epimerase activity" refers to the activity that catalyzes bilateral reactions from UDP glucose to UDP galactose and vice versa (see the formula below). UDP-glucose-4-epimerase is labeled with EC 5.1.3.2.

UDP-D-glucose ⇌ UDP-D-galactose

The term "UDP-glucose-4-epimerase activity" also refers to the aforementioned catalytic activity that is substantially the same as the activity of a protein that has the amino acid sequence as shown in SEQ ID NO: 2.

The presence of UDP-glucose-4-epimerase activity can be determined using UDP-galactose as a substrate, allowing the resulting UDP-glucose to be coupled to generation of NADH from NAD+ with the aid of UDP-glucose dehydrogenase, and measuring an increase in the absorbance at 340 nm using a spectrophotometer, with reference to, for example, the Journal of Biological Chemistry, 1964, vol. 239, 2469-2481.

The gene according to the present invention also includes DNA that hybridizes under stringent conditions to DNA consisting of the nucleotide sequence complementary to DNA consisting of the nucleotide sequence as shown in SEQ ID NO: 1 in the Sequence Listing and that encodes a protein having activity of imparting salt stress tolerance to plants.

The gene according to the present invention also includes DNA that hybridizes under stringent conditions to DNA consisting of the nucleotide sequence complementary to DNA consisting of the nucleotide sequence as shown in SEQ ID NO: 1 in the Sequence Listing and that encodes a protein having UDP-glucose 4-epimerase activity.

The term "stringent conditions" refers to conditions where what is called a specific hybrid is formed but a non-specific hybrid is not formed. Under such conditions, for example, complementary strands of DNA consisting of a highly homologous nucleic acid, i.e., DNA consisting of a nucleotide sequence exhibiting about 65% or higher, preferably about 75% or higher, more preferably about 85% or higher, and most preferably about 95% or higher, homology to the nucleotide sequence as shown in SEQ ID NO: 1 hybridize, but complementary strands of a nucleic acid having homology lower than the aforementioned level do not hybridize. More specific conditions are constituted by a sodium concentration of 150 mM to 900 mM, and preferably 600 mM to 900 mM, and a temperature of 60° C. to 68° C., and preferably 65° C.

The aforementioned deletion, addition, and substitution of amino acid residues can be carried out by modifying the aforementioned protein-encoding gene via a technique known in the art. Mutation can be introduced to a gene via conventional techniques such as the Kunkel method or the Gapped duplex method, or via a technique in accordance therewith. For example, mutation is introduced using a mutagenesis kit, such as a Mutant-K (Takara) or Mutant-G (Takara) utilizing site-directed mutagenesis or the Takara LA PCR in vitro Mutagenesis series kit (Takara).

Once the nucleotide sequence of the gene according to the present invention is determined, the gene according to the present invention can be then obtained via chemical synthesis, PCR utilizing the cloned cDNA as a template, or hybridization utilizing a DNA fragment having such nucleotide sequence as a probe. Further, modified DNA that encodes the aforementioned gene can be synthesized via, for example, site-directed mutagenesis.

2. Preparation of Recombinant Vector and Transgenic Plant (1) Preparation of Recombinant Vector The recombinant vector according to the present invention can be constructed by introducing the gene according to the present invention into an adequate vector. pBI, pUC, and pTRA vectors can be preferably used in order to introduce the gene according to the present invention into plant cells and express the gene therein. pBI and pTRA vectors can introduce the target gene into plants via *Agrobacterium*.

A pBI binary vector or intermediate vector is particularly preferable and examples thereof include pBI121, pBI101, pBI101.2, and pBI101.3. A binary vector is a shuttle vector that can replicate the gene of interest in *E. coli* and in *Agrobacterium*. When *Agrobacterium* containing a binary vector is allowed to infect plants, DNA in the portion sandwiched between border sequences consisting of the LB sequence and the RB sequence on the vector can be incorporated into the plant nuclear DNA (EMBO Journal, 10 (3), 697-704, 1991).

In contrast, a pUC vector can directly introduce a gene into plants. Examples thereof include pUC18, pUC19, and pUC9 vectors. Plant virus vectors, such as cauliflower mosaic virus (CaMV), bean golden mosaic virus (BGMV), and tobacco mosaic virus (TMV) vectors, can also be used.

The gene according to the present invention is inserted into the vector by first cleaving the purified DNA with an adequate restriction enzyme, inserting the cleavage fragment into the restriction site or multicloning site of an adequate vector DNA, and ligating the product to the vector.

The gene according to the present invention needs to be incorporated into a vector in a manner such that functions of the gene are exhibited. A promoter, an enhancer, a terminator, a poly A additional signal, a 5'-UTR sequence, or the like can be ligated to the vector at a site upstream, inside, or downstream of the gene according to the present invention.

In general, for example, a hygromycin tolerant gene, a kanamycin tolerant gene, or a bialaphos tolerant gene is necessary as a selection marker gene. In the present invention, however, a selection marker gene is not always necessary since the target clone into which the Ps UGE gene has been introduced can be selected by employing the growth conditions in galactose-containing medium as an indicator.

It is possible that the "promoter" not be derived from plants as long as the DNA can function in plant cells and can induce expression in a specific plant tissue or during a specific growth phase. Specific examples thereof include a cauliflower mosaic virus (CaMV) 35S promoter, a nopalin synthase gene promoter (Pnos), a maize ubiquitin promoter, a rice actin promoter, and a tobacco PR protein promoter.

The promoter region of a gene of which expression is known to be induced by salt stress can also be used, as well as the promoter region that is constitutively expressed in plants. Examples of such promoter include genes described in the document (Shinozaki, K., and Yamaguchi-Shinozaki, K., 2000, Molecular responses to dehydration and low temperature: Differences and cross-talk between two stress signaling pathways, Curr. Opin. Plant Biol., 3, 217-223).

An example of an enhancer is an enhancer region that is used for improving the expression efficiency of the target gene and that comprises the upstream sequence in the CaMV 35S promoter.

Any terminator can be used as long as it can terminate transcription of the gene transcribed by the aforementioned promoter. Specific examples thereof include a nopalin synthase gene terminator (Tnos) and a cauliflower mosaic virus poly(A) terminator.

(2) Preparation of Transgenic Plant

The transgenic plant according to the present invention can be prepared by introducing the recombinant vector according to the present invention into a plant in a manner such that the gene of interest (the Ps UGE gene) is incorporated in the plant gene and is expressed therein.

The gene or recombinant vector of the present invention can be incorporated in plants by, for example, the *Agrobacterium* method, the PEG-calcium phosphate method, electroporation, the liposome method, the particle gun method, and microinjection. For example, the *Agrobacterium* method may employ a protoplast or a tissue section. When a protoplast is employed, the protoplast is cultured together with the *Agrobacterium* having a Ti plasmid, or it is fused with a spheroplasted *Agrobacterium* (the spheroplast method). When a tissue section is employed, *Agrobacterium* is allowed to infect an aseptically cultivated leaf section (a leaf disc) of target plant (the leaf disc method) or a callus (an undifferentiated cultured cell).

Whether or not the gene has been incorporated into the plant can be confirmed via PCR, Southern hybridization, Northern hybridization, or other means. For example, DNA is prepared from a transgenic plant, a DNA-specific primer is designed, and PCR is then carried out. After PCR has been carried out, the amplification product is subjected to agarose gel electrophoresis, polyacrylamide gel electrophoresis, or capillary electrophoresis and stained with ethidium bromide, a SYBR Green solution, or the like, thereby detecting the amplification product as a band. Thus, transformation can be confirmed. Alternatively, the amplification product can be detected via PCR with the use of a primer that has been previously labeled with a fluorescent dye or the like. Further, the amplification product may be bound to a solid phase such as a microplate to thereby confirm the amplification product via, for example, fluorescent or enzyme reactions.

In the present invention, monocotyledonous plants or dicotyledonous plants may be used for transformation. Examples of monocotyledonous plants include those belonging to: Gramineae such as rice, barley, wheat, maize, sugarcane, Zoysia, sorghum, Italian millet, and Japanese millet; Liliaceae such as asparagus, lily, onion, *Allium tuberosum*, and Japanese dogtooth violet; and Zingiberaceae such as ginger, *Zingiber mioga*, and *Curcuma longa*. Examples of dicotyledonous plants include, but are not limited to, those belonging to: Brassicaceae such as *Arabidopsis thaliana*, cabbage, rapeseed, cauliflower, broccoli, and radish; Solanaceae such as tomato, eggplant, potato, and tobacco; Leguminosae such as soybean, garden pea, kidney bean, and alfalfa; Cucurbitaceae such as cucumber, melon, and pumpkin; Umbelliferae such as carrot, celery, and *Cryptotaenia japonica*; Asteraceae such as lettuce; Malvaceae such as cotton and okra; Chenopodiaceae such as sugar beet and spinach; Myrtaceae such as Eucalyptus and clove; and Salicaceae such as poplar.

In the present invention, examples of plant materials to be transformed include: plant tissues such as a root, stem, leaf, seed, embryo, ovule, ovary, shoot apex (the growing point at the edge of a plant seedling), anther, and pollen; sections of such plant tissues; undifferentiated calluses; and cultured plant cells such as protoplasts prepared by removing cell walls via enzyme processing.

A transgenic plant in the present invention refers to a whole plant, a plant organ (such as a root, stem, leaf, petal, seed, or fruit), a plant tissue (such as the epidermis, phloem, parenchyma tissue, xylem, vascular bundle, palisade tissue, or spongy tissue), or a cultured plant cell.

When a cultured plant cell is to be transformed, an organ or individual may be regenerated from the obtained transformed cell via conventional tissue culture techniques.

A person skilled in the art can easily carry out such procedures via a common technique that is known as a method of regenerating a plant from a plant cell. For example, a plant can be regenerated from a plant cell in the following manner.

When plant tissues or protoplasts are used as plant materials to be transformed, they are first cultured in a callus-forming medium that has been sterilized with the addition of, for example, inorganic elements, vitamins, carbon sources, saccharides as energy sources, or plant growth regulators (phytohormones, such as auxin or cytokinin), and indeterminately proliferating dedifferentiated calluses are allowed to form (hereafter, this process is referred to as "callus induction"). The thus formed calluses are transferred to a new medium containing plant growth regulators, such as auxin, and then further proliferated (i.e., subculture).

Callus induction is carried out in a solid medium such as agar, and subculture is carried out in, for example, a liquid medium. This enables both cultures to be carried out efficiently and in large quantities. Subsequently, the calluses proliferated via the aforementioned subculture are cultured under adequate conditions to induce redifferentiation of organs (hereafter referred to as "induction of redifferentiation"), and a complete plant is finally regenerated. Induction of redifferentiation can be carried out by adequately determining the type and quantity of each ingredient in the medium, such as plant growth regulators such as auxin or cytokinin, and carbon sources, light, temperature, and other conditions. Such induction of redifferentiation results in formation of adventitious embryos, adventitious roots, adventitious buds, adventitious shoots, and the like, which leads to growth into complete plants. Alternatively, such items may be stored in a state that pertains before they become complete plants (e.g., encapsulated artificial seeds, dry embryos, or freeze-dried cells and tissues).

The transgenic plant thus obtained acquires tolerance to salt stress. Accordingly, such transgenic plant can be used as a salt stress tolerant plant. The term "salt stress" used herein refers to stress caused by salts that damage physiological functions of plants. For example, salts accumulated in soil lower the water potential of the soil and plants become incapable of absorbing water. Salts include all types of salts that induce growth inhibition, lowered yield, and blight in plants. Examples thereof include sodium salt and magnesium salt.

A salt stress tolerant plant can be produced by breeding a transgenic plant in which the Ps UGE gene has been incorporated to an extent such that the resulting transgenic plant can be used as a salt stress tolerant plant. In such a case, a plant may be selected that exhibits tolerance without damage of its physiological functions, growth inhibition, or blight under the aforementioned conditions where salt stress is applied to a plant. The selected plant can be used as a stress tolerant plant at any stage after the tolerant plant has been selected.

3. Selection Marker for Transgenic Plant and Method of Selection

The gene of the present invention can be introduced into a plant and then used as a selection marker gene for a transgenic plant. The marker gene of the present invention may be introduced alone or in combination with the other target gene to be expressed.

The marker gene of the present invention may be introduced into a monocotyledonous or dicotyledonous plant. Examples thereof are as listed above, and plants capable of callus formation are preferable.

The marker gene of the present invention is introduced into, for example; plant tissues such as a root, stem, leaf, seed, embryo, ovule, ovary, shoot apex (the growing point at the edge of a plant seedling), anther, and pollen; sections of such plant tissues; undifferentiated calluses; and cultured plant cells such as protoplasts prepared by removing cell walls via enzyme processing. In the present invention, the marker gene is generally introduced into a tissue section, callus, or protoplast removed from the plant for the purpose of introduction of such gene into the plant, and the introduced marker gene is incorporated in the cell of the plant tissue, and particularly in its chromosome.

When the marker gene is introduced into a plant alone, the marker gene is ligated to a plasmid to prepare a recombinant vector. When the marker gene is introduced into a plant together with the target gene, however, the marker gene and the target gene are ligated to the same plasmid to prepare a recombinant vector. Alternatively, a recombinant vector that is obtained by ligating the selection marker gene to a plasmid may be prepared separately from a recombinant vector that is obtained by ligating the target gene to a plasmid. When recombinant vectors are separately prepared, both vectors are cotransfected into a host. During vector preparation, a promoter can be ligated to a position upstream of the target gene or the marker gene, and the terminator can be ligated to a position downstream thereof. Examples of promoters include a cauliflower mosaic virus 35S promoter, an actin promoter, and an ubiquitin promoter. An example of a terminator is a nopalin synthase gene terminator. Examples of the methods for introducing the vector into a plant include the aforementioned methods and methods similar thereto.

When the marker gene of the present invention is introduced into a plant alone, a transgenic plant having galactose tolerance can be obtained. Also, a gene that exhibits other properties, such as antimicrobial activities against given bacteria, tolerance to a given drug, the capacity for synthesizing a given useful material, sensitivity to a given phytohormone, or morphological properties different from those of the original plant, may be incorporated in the vector together with the marker gene of the present invention to obtain a redifferentiated plant exhibiting such properties.

It is preferable to form a callus from the protoplast or plant tissue into which the marker gene has been introduced in the aforementioned manner and to further culture the formed callus. Methods of callus induction, subculture, and induction of redifferentiation are as described above.

In the present invention, a transgenic plant is selected by introducing the gene or recombinant vector of the present invention into a plant, culturing the plant in a galactose-containing medium, and selecting the transgenic plant based on the presence or absence of galactose tolerance. The term "culturing" used herein includes all the culturing processes at each stage of the aforementioned "callus induction," "induction of redifferentiation," and "growth into perfect plants (rooting, gemmation, or stem extension)." Whether or not the gene has been incorporated into the plant can be confirmed by culturing the plant in the presence of galactose and inspecting the presence or absence of galactose tolerance in the cultured plant. A plant having galactose tolerance is selected as the plant into which the gene of interest has been introduced. The term "having galactose tolerance" refers to the phenomena of callus induction, induction of redifferentiation, or growth into perfect plants (e.g., rooting, gemmation, or stem extension) normally taking place, without being inhibited by galactose.

The thus selected plant may be allowed to grow into a perfect plant in accordance with the aforementioned technique that is commonly adopted in plant tissue culturing. Alternatively, such items may be stored in a state that pertains before they become complete plants (e.g., encapsulated artificial seeds, dry embryos, or freeze-dried cells and tissues).

The thus selected callus or plant has the Ps UGE gene or both the Ps UGE gene and the target gene incorporated therein. Accordingly, the presence of such gene can be confirmed via PCR or other means, and gene expression can be confirmed via RT-PCR or other means.

BEST MODES FOR CARRYING OUT THE INVENTION

Hereafter, the present invention is described in greater detail with reference to the examples, although the technical scope of the present invention is not limited thereto.

EXAMPLE 1

Cloning of Paspalum Genes, the Expression of which is Induced by Salt Stress

General RNA and DNA experiments were carried out in accordance with Molecular Cloning: A laboratory manual, second edition, Cold Spring Harbor Laboratory Press, New York, 1989. These procedures were employed as routine procedures. The method for using the kit for experiment was in accordance with the protocol issued by the manufacturer.

(1) Preparation of Plant Material

Seashore Papalum (Duedck A. E. and Peacock C. H., Agronomy Journal, vol. 77, 47-50 (1985)) was planted in a 1/5000 a Wagner pot containing sand. Seawater with a salt concentration of 2.3% to 2.7% obtained from the Tokyo Bay was poured into the pot, and culturing was carried out in a greenhouse for 3 to 6 months. Seawater was poured onto the pot once a day until it came out of the drainage hole of the Wagner pot. Through such seawater pouring, the seashore papalum kept growing for at least 5 years and exhibited tolerance to seawater.

Figure 1:
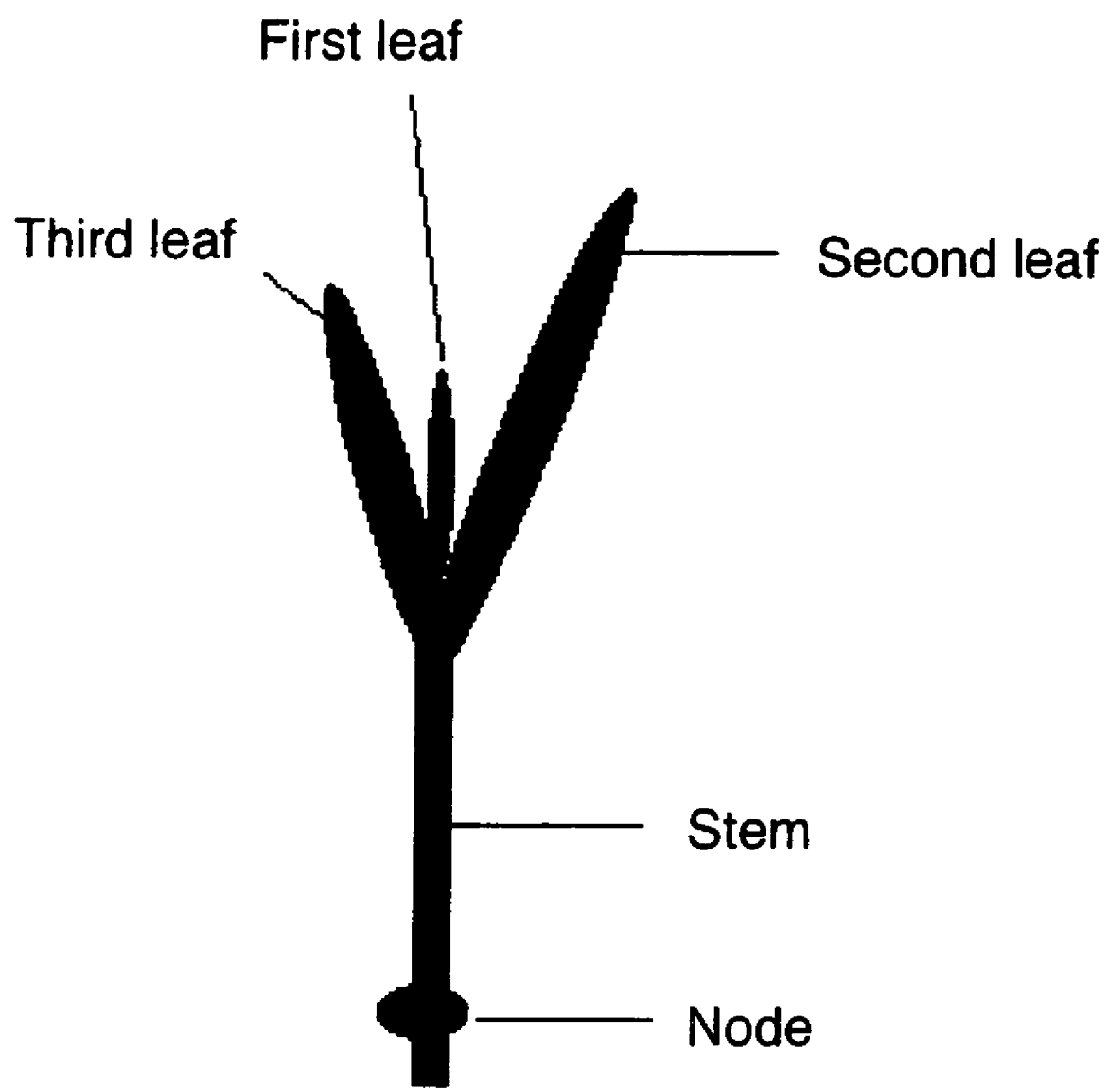
FIG. 1 shows a section containing from the first to the third leaves, the stem, and the node of seashore paspalim.

A section containing from the first to the third leaves, the stem, and the node (FIG. 1) was obtained from a branch of this material, the section was planted in the sand, the roots thereof were allowed to grow, and the cloned seedling was allowed to grow in a greenhouse. This cloned seedling was subjected to the following salt stress experiment via seawater stress application or hydroponic culture.

Seawater stress was applied in the following manner. At the outset, the grown seedling was subjected to a routine culture process in a 1/5000 a Wagner pot (soil depth: 15 cm) with the use of tap water in a greenhouse for 4 months. The soil used was a mixture of culture soil for rice and reddish soil (1:1). When the seedling was allowed to grow satisfactorily via pot cultivation (4 months after planting), the aforementioned seawater pouring was initiated.

The material of the control group was sampled before seawater pouring was initiated (tap water culturing) and then stored at $-80°$ C. The material of the salt stress group was sampled 14 days after continuous seawater pouring and then stored at $-80°$ C. The site of sampling was a leaf of the aerial part. RNAs for a cDNA library and probe preparation for differential screening as described in (3) below were extracted from the materials that had been cultured in seawater.

The salt stress experiment via hydroponic culture was carried out in the following manner. First of all, the section shown in FIG. 1 was sampled from the cloned seedling obtained via the aforementioned tap water culturing, and then planted using hydroponic water (distilled water). The resulting plant was allowed to grow and to develop roots for 1 week in a plant-growing apparatus (Cultivation Chamber CU-251, Tommy) for a light period of 16 hours (luminescence: 5000 lx; temperature: $30°$ C.) and a dark period of 8 hours (luminescence: 0 lx; temperature: $22°$ C.). After the rooting, distilled water was replaced with Yoshida's modified hydroponic medium as indicated in Table 1 (S. Yoshida, et al., Laboratory Manual For Physiological Studies of Rice 3rd. Ed., The International Rice Research Institute, pp. 61-66 (1976); trace elements: those described in D. R. Hoagland & Arnon, D.I., Univ. California Coll. Agri. c. Exp. Sta. Circ., p. 347, 1936; iron: changed with FeEDTA described in Murashige T. & Skoog F., Physiologia Plant., pp. 473-497, 1962). The plant was allowed to grow for a light period of 16 hours (luminescence: 10000 lx; temperature: $30°$ C.) and a dark period of 8 hours (luminescence: 0 lx; temperature: $22°$ C.) for 1 additional week.

After the plant had been allowed to grow, salt stress was continuously applied for 4 weeks. 500 mM NaCl was added to the aforementioned Yoshida's modified hydroponic medium and the resultant was applied to the plant as the salt stress. The leaves of the aerial part were collected 4 weeks after the salt stress application. In the Northern analysis described below in (4) and a cDNA library for isolating full-length cDNA described below in (5), RNA extracted from the section of the plant that had been hydroponically grown was used.

TABLE 1

Yoshida's modified hydroponic medium

| Component | Compound | Concentration (mg/l) |
|---|---|---|
| Nitrogen | NH$_4$NO$_3$ | 11.425 |
| Phosphoric acid | NaH$_2$PO$_4$•2H$_2$O | 50.375 |
| Potassium | K$_2$SO$_4$ | 89.25 |
| Calcium | CaCl$_2$•H$_2$O | 146.625 |
| Magnesium | MgSO$_4$•7H$_2$O | 405 |
| Iron (Fe EDTA) | FeSO$_4$•7H$_2$O | 9.964 |
| | Na$_2$•EDTA | 13.36 |
| Trace elements | MnCl$_2$•4H$_2$O | 2.213 |
| | ZnSO$_4$•7H$_2$O | 0.22 |
| | H$_3$BO$_4$ | 2.875 |
| | CuSO$_4$•5H$_2$O | 0.08 |
| | Na$_2$MoO$_4$•2H$_2$O | 1.21 |
| Buffer | MES | 2137 |

The pH level of the hydroponic medium was adjusted to 5.5 with the use of 5N NaOH. The volume of the hydroponic medium was inspected every 2 days. When the volume decreased, distilled water was added thereto to bring the volume back to the initial level (i.e., 4 l in the case of a Wagner pot). The hydroponic medium was exchanged with fresh medium once every 2 weeks.

(2) Preparation of RNA and Construction of cDNA Library

Total RNA (about 1 mg) was extracted from 2 g of leaves (fresh weight) using the Rneasy Mini Kit (Qiagen) or in accordance with the method of Chang, S. et al. (Plant Mol. Biol. Report, 11, pp. 113-116, 1993). DNase I treatment was additionally carried out in each case with the use of RNase-free (TaKaRa Bio Inc.) in the presence of 5 mM MgSO$_4$ at 25° C. for 11 hours. Further, 10 μg of mRNA was separated and purified from total RNA using the BioMag SelectaPure mRNA Purification System (Polysciences, Inc.). The first strand cDNA and the second strand cDNA were synthesized from 5 μg of mRNA using oligo(dT)$_{12-18}$ and the Time Saver cDNA synthesis kit (Amersham Biosciences). Subsequently, cDNA was inserted into a λgt11 phage vector using the directional cloning kit (Amersham Biosciences) for cDNA cloning, and the resultant was packaged using the Ready-To-Go Lambda Packaging Kit (Amersham Biosciences). *E. coli* Y1088 was used as a host cell, the titer was examined, and differential screening was then carried out.

(3) Preparation of Probe and Differential Screening

The aforementioned seashore paspalum was hydroponically grown with tap water for 4 months from the state of herbaceous cutting (the control group). Separately, the seashore paspalum was allowed to grow for 4 months and seawater was then continuously applied thereto for 2 weeks (the salt stress group). Total RNA was prepared therefrom, and the first strand cDNA was prepared using oligo (dT)$_{12-18}$ and the Time Saver cDNA synthesis kit (Amersham Biosciences). The resulting first strand cDNA was used as a template and PCR was carried out using the random hexamer (pdN$_6$) included in the kit (PCR conditions: cDNA was subjected to thermal denaturation at 94° C. for 5 minutes using the premix ExTaq (TaKaRa Bio Inc.), 25 cycles of 94° C. for 30 seconds, 55° C. for 1 minute, and 72° C. for 1 minute, followed by 72° C. for 1 minute, with the use of the Gene Amp PCR System 9600. The PCR product was subjected to gel electrophoresis and two types of probes (i.e., the control probe and the salt stress probe) were prepared using the ECL direct labeling kit (Amersham Biosciences). cDNA libraries were sowed on a 14.5-cm petri dish, and 2,000 plaque samples were subjected to differential screening. Plaque blotting was carried out using Hybond N (Amersham Biosciences), and the plaque signals were detected using the ECL detection system (Amersham Biosciences). The 2 aforementioned types of probes were subjected to detection of each sheet, and plaque samples that were detected with the salt stress probe but were not detected with the control probe were selected as plaque samples specific for the salt stress group.

Phage DNA was extracted in order to transfer the insert region of the selected clones into a plasmid vector. Phage DNA was treated at 94° C. for 10 minutes and then quenched. PCR was carried out using the resulting phage DNA as a template, the λgt11 forward primer (5'-GGT GGC GAC GAC TCC TGG AGC CCG-3': SEQ ID NO: 3) and reverse primer (5'-TTG ACA CCA GAC CAA CTG GTA ATG-3': SEQ ID NO: 4) (Takara Bio Inc.), and Premix ExTaq (Takara Bio Inc.) (95° C. for 1 minute, 25 cycles of 94° C. for 1 minute, 55° C. for 2 minutes, and 72° C. for 2 minutes, followed by 72° C. for 2 minutes). The resulting PCR product was subcloned into the pT7 Blue T-vector using the Perfectly Blunt® Cloning Kit (Novagen). Pluralities of selected clones were subjected to sequencing in accordance with the dRhodamine dye-terminator method (AmpliTaq DNA polymerase FS; Applied Biosystems), and the DNA sequence was then bilaterally determined using the ABI 310 genetic analyzer (Applied Biosystems).

(4) Secondary Screening via Northern Analysis (Comparison with Rice)

Probes for secondary selection were prepared from the 2 obtained clones (Ps ABA and Ps uge). The Ps ABA probe was prepared by cleaving the cloning site of the pT7 Blue T-vector with the restriction enzyme EcoRI (Takara Bio Inc.) and the insert region with the restriction enzyme AluI (New England Biolab) so as not to contain poly A, and cleaving out the fragment via agarose electrophoresis (SEQ ID NO: 5). The Ps UGE probe was prepared by subcloning the cDNA clone Ps uge (SEQ ID NO: 6) obtained via the first differential screening into the pT7 T-vector and cleaving out the fragment at the NotI site and the ScaI site in the insert region (SEQ ID NO: 7).

Ps ABA probe (SEQ ID NO: 5):

```
TGCCGTGGGCTCCGGCGGGTTCGCCTTCCACGAGCACCACGAGAAGAAGG
AGGACCACAAGGACGCCGAGGAGGCCGGCGGCGAGAAGAAGCACCACTTC
TTCGGCTGATCCATCTCACCATCTCCATCTCCCACCCCCATCGATCCATT
TGTGTTGGCTTTAATTCCCTGCGTGCATGCGTGTTGTTGAATAAGGGGCC
GGTTCCATCTGTACGTACGTGTACTCCGAGACCTATCGTCATGTGTGTGT
GTGTACGTATACCTGCTGTGTACATGATGGTCGTATATGCCACTGGACTA
TGTGTGTGTGCAACTCTGTTCTGATTTGCTATATATAAG
``` cDNA clone Ps uge obtained via the first differential screening (SEQ ID NO: 6):

```
TGCAGGGACCAGTGGAACTGGGCCAAGAAGAACCCCTATGGCTACTGCGG
CACTGCCGAAAAATAGAGCGCGTGCATTAATCAGATCTCTGGACTGAATT
TGTCCATGGTTGATGGTTGTCTCAGACCTATCGGTGGAAGATGTAACAAG
TAGAGACCGCTCGAATGTGCCTAGCTACGAAGTTTCGTACCATCTCTCTT
GTCATAACCTCATGTAGATGGTCATTTTATTGGAATTAGCCTTAGCCTTC
```

-continued

AGGCCCGGCGCTGTTAAAATTTGTTTTACACATGGATTTTCTCGCTACGT

GTGATACATATTGTGTCTGTAATAATCCTGATCGGAGTTTCCAGTAATAA

AACCGATCCACGACGGTGGCTACGCCCTGTGTTGTAGTactgtgaatatg atgtggtaataacaataacttgcagtgagacttcagctttcaaaaaaaaa aaaaaaaaaaaaaaaaaaaaaaaaaaaaaaaaaaaaaaaaaaaaaaaa Ps UGE probe (SEQ ID NO: 7):

GGCCGCTGTGCAGGGACCAGTGGAACTGGGCCAAGAAGAACCCCTATGGC

TACTGCGGCACTGCCGAAAAATAGAGCGCGTGCATTAATCAGATCTCTGG

ACTGAATTTGTCCATGGTTGATGGTTGTCTCAGACCTATCGGTGGAAGAT

GTAACAAGTAGAGACCGCTCGAATGTGCCTAGCTACGAAGTTTCGTACCA

TCTCTCTTGTCATAACCTCATGTAGATGGTCATTTTATTGGAATTAGCCT

TAGCCTTCAGGCCCGGCGCTGTTAAAATTTGTTTTACACATGGATTTTCT

CGCTACGTGTGATACATATTGTGTCTGTAATAATCCTGATCGGAGTTTCC

AGTAATAAAACCGATCCACGACGGTGGCTACGCCCTGTGTTGTAGT

The prepared Ps ABA probe and the Ps UGE probe were used to compare the gene expression inducibility by salt stress of Paspalum and rice (variety: Pokkari). The clones, the expression of which is induced by salt stress in Paspalum but is not induced in rice, were subjected to secondary selection. Rice (variety: Pokkari) was allowed to grow in the aforementioned Yoshida's modified hydroponic medium, and total RNA was extracted from the shoots of the control group (0 mM NaCl) and the salt stress group (50 mM NaCl) 1 month later. Electrophoresis of total RNA, Northern blotting, and hybridization were carried out in accordance with conventional techniques.

Through Northern analysis using the Ps ABA probe, mRNA detected with the Ps ABA probe was found to be expressed in total RNA of both Paspalum and rice, and expression was found to be induced by salt stress (FIG. 2A). Accordingly, this Ps ABA clone was not selected, since a homolog thereof was expressed in rice with lower salt tolerance. In contrast, Northern analysis using the Ps UGE probe demonstrated that the expression of Ps UGE was induced by salt stress in Paspalum but was not induced in rice (variety: Pokkari) (FIG. 2B). Accordingly, this Ps UGE clone was selected as a clone specific for Paspalum. Homology search of the DNA sequence of the Ps UGE probe was carried out with Blast X. As a result, such sequence was found to be homologous to the gene of Guar (Cmopsis tetragonoloba) (Accession No. AJ005081, Joersbo, M., et al., Plant Science 142, pp. 147-154, 1999) and the gene of Arabidopsis thaliana (Dormann, P. & Benning, C., Archives of Biochemistry and Biophysics, 327, pp. 27-34, 1996). This Ps UGE clone was utilized as a probe for full-length cDNA isolation.

(5) Isolation and Sequence Determination of Full-Length cDNA mRNA (10 μg) was obtained from Paspalum to which salt stress (400 mM NaCl) had been applied through Yoshida's hydroponic medium over the period of a week, and synthesis of cDNA, cloning into the Zap Express vector, and packaging were carried out using the ZAP Express cDNA Gigapack III Gold Cloning kit (Stratagene). cDNA libraries were sowed on 10 rectangular petri dishes (14 cm×9 cm), and about 100,000 plaque samples were subjected to selection. Plaque blotting was carried out using Hybond N (Amersham Biosciences), the Ps UGE probe used in Northern analysis in (4) above was labeled with the ECL direct labeling kit (Amersham Biosciences), and plaque signals were detected using the ECL detection system (Amersham Biosciences). As a result of the primary to the tertiary screening procedures, 3 plaque samples for which detection took place with the Ps UGE probe were isolated. Each cDNA was transferred into the pBK-CMV phagemid vector (Stratagene) via in vivo excision. The 3 selected cDNAs were subjected to sequencing by the dRhodamine dye-terminator method (AmpliTaq DNA polymerase FS: Applied Biosystems), and the DNA sequence was then determined bilaterally using the ABI 310 Genetic Analyzer (Applied Biosystems). T7 and T3 primers and primers specific for each of the cDNAs were used for sequencing. Sequence analysis was carried out using Genentyx Mac. Ver. 11 (Software Development Co. LTD, 2000).

As a result of sequencing, a cDNA clone (Ps UGE1) that was substantially consistent with the sequence of Ps UGE was obtained. The nucleotide sequence of Ps UGEI is shown in SEQ ID NO: 1, and the amino acid sequence encoded thereby is shown in SEQ ID NO: 2. Also, a cDNA clone (Ps UGE2) exhibiting 65% homology to Ps UGE1 at the amino acid level was obtained. The nucleotide sequence of Ps UGE2 is shown in SEQ ID NO: 8, and the amino acid sequence encoded thereby is shown in SEQ ID NO: 9.

(6) Comparison with UGE Homolog Derived from other Species

Figure 3:
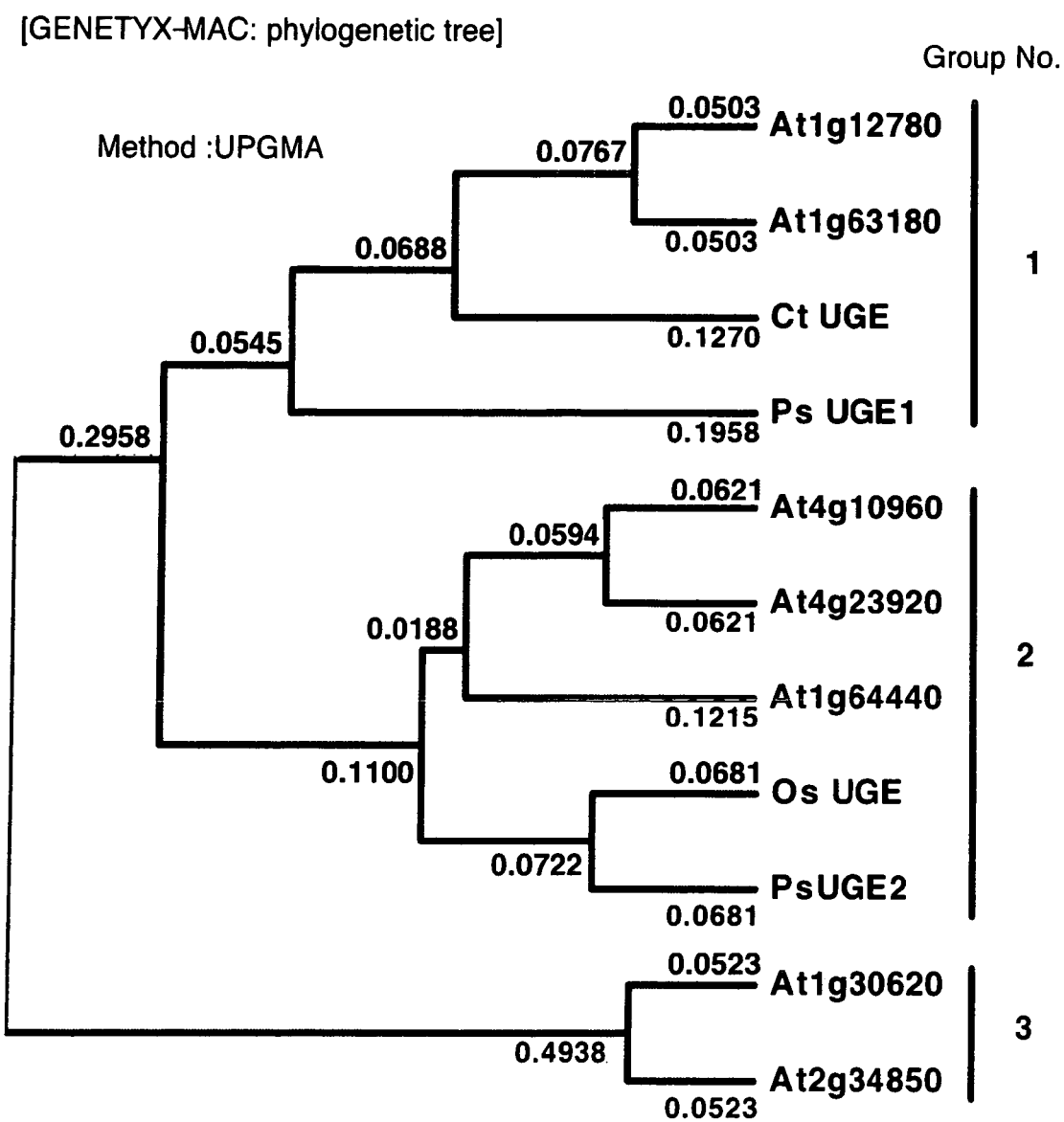
FIG. 3 shows a phylogenetic tree of the UGE homologues derived from plants in relation to Ps UGE1 and Ps UGE 2 (comparison of amino acid sequences).

A phylogenetic tree of the plant UGE homologues that had been registered in the past based on EST and genomic analysis, Ps UGE1, and Ps UGE2 was prepared (FIG. 3; UGE families of Arabidopsis thaliana, At1g30620, At1g12780, At1g63180, At1g64440, At2g34850, At4g10960, and At4g23920, rice Os UGE (Accession No. AB087745), and guar Ct UGE (Accession No. AJ005081) were used). Based thereon, Ps UGEI was classified into group No. 1. The results of amino acid sequence alignments of the homologues classified into group No. 1 and Ps UGE2 are shown in FIG. 4. Ps UGE1 had a novel feature, i.e., the N-terminal amino acid sequence was longer by approximately 10 nucleotides than the UGE gene of Arabidopsis thaliana, which is considered to be a so-called orthologue of group No. 1, and than Ps UGE2 derived from the same paspalum (FIG. 4).

EXAMPLE 2

Preparation of Vector for Plant Expression

The full-length cDNA of Ps UGE obtained in Example 1 was introduced into an expression vector for introducing plant genes in the following manner. In order to remove the 3'-poly(A), PCR was carried out using the aforementioned clone PS UGE1 as a template, the sequence consisting of a 45-bp to 64-bp region upstream of the insert 5'-ACAGAGC-CGCAAAACCACAC-3' (SEQ ID NO: 10), as the sense primer, the sequence consisting of a 1314-bp to 1340-bp region downstream thereof 5'-TTCGTAGCTAGGCACAT-TCGAGCGGTC-3' (SEQ ID NO: 11), as the antisense primer, and the Pyrobest enzyme (Takara Bio Inc.) under conditions of 98° C. for 2 minutes, 30 cycles of 96° C. for 30 seconds, 62° C. for 30 seconds, and 72° C. for 2 minutes, followed by 72° C. for 3 minutes. The amplified DNA fragment (about 1.3 kb) was separated via agarose gel electrophoresis, cleaved out, and then purified using a Gel Extraction Kit (Qiagen). This fragment was cloned into pCR-Script Amp SK(+) using the PCR-Script Amp Cloning Kit (Stratagene) and subjected to sequencing to determine the sequence thereof The pCR-Script Amp SK(+) clone having this 1.3-kb fragment as an insert was designated as Ps UGE1a.

Ps UGE1a was treated with the restriction enzyme NotI (Toyobo Co., Ltd.), subjected to ethanol precipitation, blunt-ended using a Blunting Kit (Takara Bio Inc.), and then purified via phenol extraction. Further, this fragment was treated with BamHI (Toyobo Co., Ltd.), and the cleaved fragment of the PS UGE gene (about 1.3 kb) was separated via 0.7% agarose gel electrophoresis, followed by purification using a Gel Extraction Kit (Qiagen).

Figure 5:
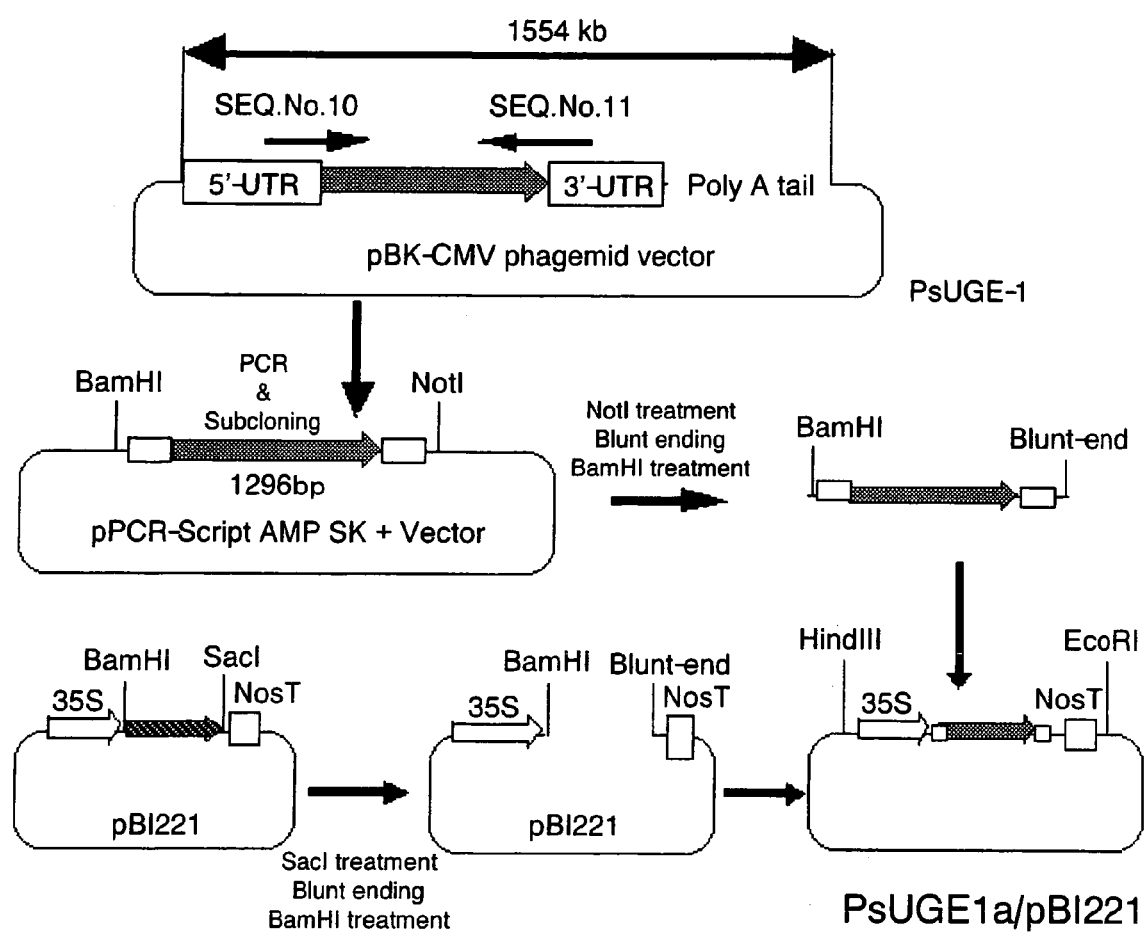
FIG. 5 shows a procedure for constructing a plant expression vector Ps UGE1a/pBI221.

In order to insert the gene fragment between a promoter and a terminator, pBI221 (Clontech) was treated with the restriction enzyme SacI (Toyobo Co., Ltd.) and then subjected to ethanol precipitation. Subsequently, the SacI cleavage site was blunt-ended using the Blunting Kit (Takara Bio Inc.), followed by purification via phenol extraction. This fragment was further treated with BamHI (Toyobo Co., Ltd.), a vector portion was separated from the GUS portion via 0.7% agarose gel electrophoresis, and a vector fragment was purified using a Gel Extraction Kit (Qiagen). Thereafter, the Ligation Kit ver. 1 (Takara Bio Inc.) was used to ligate the vector portion to the UGE gene fragment (about 1.3 kb), the ligation product was transformed into E. coli JM109, and a clone into which the Ps UGE gene fragment (about 1.3 kb) had been inserted in a sense direction in relation to the promoter region was selected. The selected clone was designated as Ps UGE1a/pBI221. The aforementioned construction procedure is shown in FIG. 5.

The following operation was carried out in order to insert the Ps UGE1a/pBI221 expression cassette portion into a binary vector for gene introduction. Ps UGE1a/pBI221 was processed with the restriction enzyme EcoRI (Toyobo Co., Ltd.), subjected to ethanol precipitation, blunt-ended using a Blunting Kit (Takara Bio Inc.), and then purified via phenol extraction. Further, this DNA was processed with the restriction enzyme HindIII (Toyobo Co., Ltd.), subjected to ethanol precipitation, and processed with DraIII (New England Biolab). The 35S:Ps UGE:nos T expression cassette portion (about 2.5 kb) was separated from the vector portion via 0.7% agarose gel electrophoresis, and the expression cassette portion was purified using a Gel Extraction Kit (Qiagen). Subsequently, the pIG121Hm vector (Plant Cell Report, Vol. 12, pp. 7-11, 1992, obtained from Mr. Kenzo Nakamura at Nagoya University) was processed with the restriction enzyme SalI (Toyobo Co., Ltd.) and then subjected to ethanol precipitation. Subsequently, the SalI cleavage site was blunt-ended using a Blunting Kit (Takara Bio Inc.) and then purified via phenol extraction. This plasmid vector fragment was processed with the restriction enzyme HindIII (Toyobo Co., Ltd.), the vector portion was separated from the 35S:Intron-GUS:nos T portion via 0.7% agarose gel electrophoresis, and a vector fragment was purified using a Gel Extraction Kit (Qiagen). Thereafter, the fragment of the Ps UGE gene expression cassette was ligated to the vector fragment using the Ligation Kit ver. 1 (Takara Bio Inc.), a clone into which the fragment of the Ps UGE gene expression cassette had been inserted at the plasmid vector pIG121Hm 35S:Intron-GUS:nos T portion was selected, and the selected clone was designated as Ps UGE1a/pBI 121 Hm.

Ps UGE1a/pBI121Hm was processed with the restriction enzyme BamHI (Toyobo Co., Ltd.), subjected to ethanol precipitation, blunt-ended using a Blunting Kit (Takara Bio Inc.), and then purified via phenol extraction. This fragment was further processed with HindIII, a DNA fragment of the Ps UGE1a expression cassette +35S:hygromycin tolerant (HPT) gene was cleaved via 0.7% agarose electrophoresis, and purified using a Gel Extraction Kit (Qiagen). pBI221 (Clontech) was processed with the restriction enzyme SacI (Toyobo Co., Ltd.), subjected to ethanol precipitation, blunt-ended using a Blunting Kit (Takara Bio Inc.), and then purified via phenol extraction. This fragment was further processed with HindIII (Toyobo Co., Ltd.), the vector portion was separated from the 35S:GUS portion via 0.7% agarose gel electrophoresis, and the vector fragment was purified using a Gel Extraction Kit (Qiagen). The Ligation Kit ver. 1 (Takara Bio Inc.) was used to ligate the vector portion to the Ps UGE1a expression cassette +35S:HPT gene, the ligation product was transformed into E. coli JM109, and a clone into which the Ps UGE gene fragment (about 1.3 kb) had been inserted in a sense direction in relation to the promoter region was selected. The selected clone was designated as Ps UGE1a/pBI221Hm.

pIG121Hm was processed with the SalI and BamHI (Toyobo Co., Ltd.), the vector portion was separated from the 35S:HPT gene portion via 0.7% agarose gel electrophoresis, and the 35S:HPT gene portion was cleaved and then purified using a Gel Extraction Kit (Qiagen). The resultant was further blunt-ended using a Blunting Kit (Takara Bio Inc.). Subsequently, pBI221 was processed with HindIII and SacI, separated via 0.7% agarose gel electrophoresis, and a vector fragment was purified using a Gel Extraction Kit (Qiagen). This vector fragment was further blunt-ended using a Blunting Kit (Takara Bio Inc.), and ligated to the aforementioned 35S:HPT gene portion using the Ligation Kit ver. 1 (Takara Bio Inc.). After transformation into E. coli JM109, a ligation product comprising a 35S promoter, an HPT gene, and a Nos terminator ligated in that order was selected and designated as HPT/pBI221. The product was used for cotransformation with Ps UGE1a/pBI221.

EXAMPLE 3

Preparation of Transgenic Plant (Rice) and Confirmation of Introduced Gene (1) Preparation of Ps UGE Transgenic Rice Protoplast was isolated from a liquid culture system capable of redifferentiation derived from ripe rice seeds (variety: Nipponbare; seed paddies available from the Agricultural Cooperatives in Shiga) and designated as a test material. Protoplast preparation and electroporation were carried out in accordance with, for example, the method of Kyozuka et al. (Mol. Gen. Gnet., 206, pp. 408-413, 1987), the method of Toriyama et al. (Bio/Technology 6, pp. 1072-1074), or the method of Akagi et al. (Mol. Gen. Gnet., 215, pp. 501-506, 1989).

The protoplast ($2\times10^6$/ml) and plasmid DNA (cotransformation of Ps UGE1a/pBI121Hm, Ps UGE1a/pBI221Hm, or Ps UGE1a/pBI221 with HPT/pBI221) were suspended in an introduction buffer to a concentration of 50 µg/ml comprising 0.4 M mannitol, 70 mM potassium aspartate, 5 mM calcium gluconate, and 5 mM MES and then subjected to electroporation. The electrical pulse used was a damped wave with a field intensity of 450 V/cm and a time constant of about 40 ms. The apparatus used for introduction was GTE-10 and the introduction chamber was FTC-54 (Shimadzu).

Protoplasts embedded in an agarose medium prepared based on R2P medium (Ko Shimamoto and Kiyotaka Okada (edit.), *Shokubutsu saibo kogaku* (Plant Cell Technology) Series, *Moderu Shokubutsu no jikken purotokoru* (Model plant protocol), pp. 82-88, 2001, Shujunsha) were added to liquid medium and cultured together with nurse cells. Nurse cells and the liquid medium were removed 14 days after introduction, a R2P medium comprising 50 µg/ml hygromycin was added, and selection of transgenic plants was initiated. After tolerant calluses had been allowed to grow to 1 mm to 2 mm, the selected transgenic calluses were transferred to an R2SA medium comprising 50 µg/ml hygromycin (Ko Shimamoto et al., as above, p. 83). The transgenic calluses were cultured for 10 to 14 days and allowed to multiply, and the calluses were transferred to a redifferentiation medium comprising 50 µg/ml hygromycin (Ko Shimamoto et al., as above, pp. 78-81) to regenerate plants.

The redifferentiated plants were separated from the callus mass and were then transferred to a hormone-free medium comprising 50 µg/l hygromycin (Ko Shimamoto et al., as above, pp. 78-81). Rooting plants were selected, the lid of the petri dish was opened to pour sterilized water on the medium therein, and plants were allowed to acclimate for 1 week. At this time, sterilized water was supplied once every 2 days in order to keep the medium moistened. After the acclimation, the selected plants (the T0 generation of Nipponbare) were planted in a Jiffy pot (5 cm (breadth)×5 cm (width)×6 cm (height)) containing culture soil for rice (Mitsubishi Chemical Corporation) and spherical reddish soil (1:1), transferred to a plastic pot (15 cm (width)×5.5 cm (depth)×9.5 cm (height)) 1 to 2 months thereafter, and further allowed to grow for 4 to 10 months. Seeds were obtained via self-fertilization or crossing. Plants were allowed to grow in an isolated greenhouse.

(2) Confirmation of Introduction and Expression of the Ps UGE gene

Genomic DNA was extracted from the transgenic rice by cutting the young leaves into 1- to 3-cm length pieces, placing them into a sterilized Eppendorf tube, adding 100 µl of TE buffer (10 mM Tris HCl, pH 8.0, 1 mM EDTA), and grinding the leaves with a homogenizer for Eppendorf tubes for 1 to 3 minutes. The ground leaves were stored on ice and centrifuged at 4° C. and 15,000 rpm for 2 minutes. The supernatant was transferred to a new sterilized tube. This supernatant was designated as a genomic DNA fraction.

In order to confirm the presence of the Ps UGE gene, genomic PCR was carried out using the sequence: 5'-GTC GTC GAC AAC TTC CAC AA-3' (SEQ ID NO: 12) as a sense primer, the sequence: 5'-TTG TTC TCG TAG TAC ATG TC-3' (SEQ ID NO: 13) as an antisense primer, 1.25 U of KOD Dash polymerase (Toyobo Co., Ltd.), 10 pmoles of primers, 0.2 mM dNTP, and a reaction buffer (final concentration: 20 mM Tris-HCl (pH7.5), 8 mM MgCl$_2$, 7.5 mM DTT, 2.5 µg/50 µL BSA). The aforementioned genomic DNA was used in an amount of 10 µl in relation to the total amount (i.e., 20 µl) of the PCR reaction solution. The Gene Amp PCR System 9600 or Gene Amp PCR System 9700 (ABI) was used. PCR was carried out at 98° C. for 2 minutes, for 30 cycles of 98° C. for 30 seconds, 55° C. for 2 seconds, and 74° C. for 30 seconds, and 74° C. for 5 minutes. The temperature was then maintained at 4° C.

Figure 6:
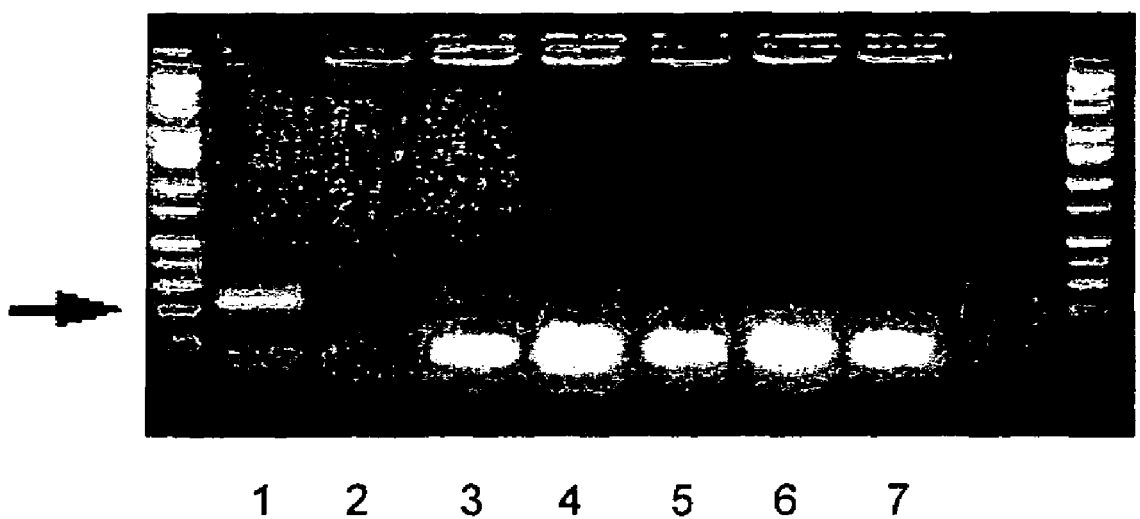
FIG. 6 shows the results of detecting the Ps UGE genes in various rice plant varieties via genomic PCR (lane 1: a vector; lane 2: a non-transgenic Nipponbare; lane 3; the Ps UGE transgenic rice; lane 4: Nipponbare; lane 5: IR28; lane 6: Koshihikari; and lane 7: Pokkari). An arrow points to the position of a band corresponding to a 226-bp internal sequence of the Ps UGE gene.

The results of genomic PCR are shown in FIG. 6. As shown in FIG. 6, the 226-bp fragment amplified by using the sequence as shown in SEQ ID NO: 12 as the sense primer and the sequence as shown in SEQ ID NO: 13 as the antisense primer (lane 1: vector DNA) was detected exclusively in the Ps UGE transgenic Nipponbare (lane 3). It was not detected in any non-transgenic rice varieties (Nipponbare (lanes 2 and 4), Koshihikari (lane 6), IR28 (lane 5), or Pokkari (lane 7)). This indicates that such fragment is suitable for confirming transgenic plants. FIG. 7 shows the results of genomic PCR similarly carried out concerning the T0 generation of the Ps UGE transgenic Nipponbare (the plant into which the gene had been introduced and selected) and the F1 generation resulting from the crossing of the T0 generation and Koshihikari. In FIG. 7, an arrow points to the position of a band corresponding to a 226-bp internal sequence of the Ps UGE gene, V indicates a PCR product obtained when the expression vector Ps UGE1a/pBI221 is used as a template, and NT indicates a genomic PCR product of a non-transgenic rice plant. As shown in FIG. 7 (upper portion), bands indicating the presence of the Ps UGE gene were observed in 20 out of the 22 individuals of the T0 generation of hygromycin tolerant plants. Concerning the F1 generation resulting from the crossing of the T0 generation of Nipponbare plants and non-transgenic Koshihikari, the presence of the Ps UGE gene was observed in the genomes of 29 out of the 46 individuals (FIG. 7, lower portion). Bands indicating the presence of the Ps UGE gene were finally observed in 106 out of 120 individuals of the T0 generation of hygromycin tolerant rice plants. Among a total of 193 individuals of the F1 generation, the presence of the Ps UGE gene was observed in 90 individuals.

In order to confirm transcription of the Ps UGE gene introduced into the T0 generation of the Ps UGE transgenic Nipponbare plants, RT-PCR was carried out using the sequence (SEQ ID NO: 12, as shown above) as a sense primer, the sequence (SEQ ID NO: 13, as shown above) as an antisense primer, 1.25 U of KOD Dash polymerase (Toyobo Co., Ltd.), 10 pmoles of primers, 0.2 mM dNTP, and a reaction buffer (final concentration: 20 mM Tris-HCl (pH7.5), 8 mM MgCl$_2$, 7.5 mM DTT, 2.5 µg/50 µL BSA). The first strand cDNA prepared from the aforementioned total RNA using the 1st strand cDNA synthesis kit (Life Science) was used in an amount of 0.2 to 10 pi in relation to the total amount (i.e., 20 µl) of PCR reaction solution. The Gene Amp PCR System 9600 or Gene Amp PCR System 9700 (ABI) was used. PCR was carried out at 98° C. for 2 minutes, for 30 cycles of 98° C. for 30 seconds, 55° C. for 2 seconds, and 74° C. for 30 seconds, and 74° C. for 5 minutes. The temperature was then maintained at 4° C.

The results of RT-PCR are shown in FIG. 8. In FIG. 8, an arrow points to the position of a band corresponding to a 226-bp internal sequence of the Ps UGE gene, V indicates a PCR product obtained when the expression vector Ps UGE1a/pBI221 is used as a template, and NT indicates an RT-PCR product when the first strand cDNA of a non-transgenic rice plant is used as a template. As shown in FIG. 8, bands indicating the transcription of the Ps UGE gene were observed in 20 out of the 22 individuals of the T0 generation of hygromycin tolerant plants, when cDNA was used as a template. In contrast, no band was observed regarding the total RNA used for the synthesis of the first strand cDNA. This indicates that the band observed is not derived from genomic DNA. As a result of RT-PCR thus performed, 95 individuals of the T0 generation of Npponbare plants were found to express Ps UGE among the 106 hygromycin tolerant rice individuals (T0 generation) comprising Ps UGE in their genomes. Further, expression of the Ps UGE gene was observed in 81 individuals of the F1 generation plants (plants resulting from the crossing of the T0 generation of Nipponbare plants and Koshihikari) among the 90 F1 individuals comprising Ps UGE in their genomes.

EXAMPLE 4

Confirmation of UDP-Galactose Epimerase Activity

Leaf blades (0.1 g to 0.15 g) were removed from individuals of the T0 generation of the Ps UGE transgenic rice obtained in Example 3, plants redifferentiated from non-transgenic rice calluses as the rice control group that does not express the Ps UGE gene, or individuals of the T0 generation of the transgenic rice that expresses sGFP under the control of 35S. The leaf blades were frozen with liquid nitrogen and then preserved at −80° C. An extraction buffer (1 tablet of protease inhibitor cocktail, Complete, Mini (Roche) dissolved in 7 ml of a buffer comprising 25 mM Hepes (pH 7.5), 0.3 M sorbitol, and 5 mM DTT) was added to leaves in amounts of 1 to 1.5 ml in relation to 0.1 to 0.15 g of fresh leaves, a spoonful of Polychlal AT and a spoonful of quartz sand were added thereto, and the resulting mixture was ground quickly on ice in a mortar. When the mixture became a solution, the solution was transferred to a 2-ml Eppendorf tube, and centrifugation was carried out at 15,000 rpm and 4° C. for 20 minutes. The supernatant was transferred to another tube, and the total amount in the tube was brought to 1 ml with an extraction buffer. The resulting liquid (1 ml) was applied to an NAP-10 column (Amersham Biosciences) and eluted with 1.5 ml of extraction buffer, followed by desalting. In the case of the Ps UGE transgenic rice, 40 μl out of 1.5 ml of the desalted eluate was subjected to activity assay. In the case of a non-transgenic plant or a transgenic rice plant (T0 generation) that expresses sGFP, 1.5 ml of the eluate was placed in an YM-10 concentrator (Centricon, Millipore) and concentrated to 0.3 ml via centrifugation at 6,000 rpm (Hitachi Himac) and 4° C. for 120 minutes. 40 μl thereof was then subjected to activity assay. The amount of protein was quantified using a protein assay kit (Bio-Rad).

Activity was assayed in the following manner. At the outset, 40 μl of the aforementioned enzyme solution was added to 0.46 ml of a reaction solution (blank) containing 50 mM Tris HCl (pH 8.5) and 1 mM NAD+, and increases in the absorbance at 340 nm at 28° C. were assayed for 3 minutes to determine the slope (Δabs 1/min) of the blank. The absorbance was assayed using a Beckman DU-640 spectrophotometer. Subsequently, 40 μl of the aforementioned enzyme solution was added to 0.46 ml of a reaction solution containing 50 mM Tris HCl (pH 8.5), 1 mM NAD+, and 0.5 mM UDP-galactose, and increases in the absorbance were similarly assayed to determine the slope Δabs 2/min. Based on the value ΔA340/min obtained by subtracting Δabs 1/min from Δabs 2/min, specific activity was determined using the following equation.

Specific activity (mU/mg protein)=[ΔA340/min×the amount of reaction solution (ml)÷6220 (M$^{-1}$·cm$^{-1}$)]÷the amount of enzyme solution (ml)÷the protein content in the enzyme solution (mg/ml)× 1000

The specific activity (mU/mg protein) of the 3 rice lineages was assayed, and the mean and the standard deviation were determined. As a result, specific activity was found to be 37.7±5.5 in the Ps UGE transgenic rice, 4.1±1.8 in the plants redifferentiated from the calluses of non-transgenic rice plants, and 2.8±0.8 in the sGFP transgenic rice. Specifically, UDP-galactose epimerase activity of the Ps UGE transgenic rice was found to be 8 to 10 times higher than that of rice that does not express the PsUGE gene. Also, the PsUGE gene was found to have UDP-galactose epimerase activity or UDP-glucose epimerase activity.

EXAMPLE 5

Examination of Galactose Tolerance of Ps UGE Transgenic Rice Plant

The Ps UGE transgenic rice (35S:Ps UGE1a:nosT) obtained in Example 3 and plants redifferentiated from the calluses of non-transgenic rice plants (Nipponbare, the control) were used to inspect the influence of galactose and the effects of Ps UGE on rooting. Culturing was carried out in a medium modified from the antibiotic-free test medium MSHF (Shuji Yokoi et al., same as the above) in which the sucrose content was altered to 0 mM and the galactose content was altered to 21 mM, 42 mM, 84 mM, or 168 mM, or in a medium in which the glucose content was altered to 21 mM, 42 mM, 84 mM, or 168 mM for a 16-hour photoperiod at 10000 lx for 1 to 2 weeks. The results of culturing are shown in FIG. 9. In the case of the plants redifferentiated from the calluses of non-transgenic rice plants, rooting takes place in a medium with a high glucose content in substantially the same manner as in a medium containing sucrose. However, rooting was completely inhibited in the medium with a high galactose content. In contrast, inhibition of rooting caused by galactose was substantially completely eliminated in Ps UGE transgenic rice plants (35S:Ps UGE1a:nosT) (FIG. 9). FIG. 10 shows a photograph of the rooting of the Ps UGE. transgenic rice (35S:Ps UGE1a:nosT) and of the plants redifferentiated from the calluses of non-transgenic rice plants, when they are allowed to grow in a medium containing galactose. It also shows the number of adventitious roots and the maximal lengths of adventitious roots (cm). FIG. 11 shows a photograph of the shoots of the Ps UGE transgenic rice (35S:Ps UGE1a:nosT) and of the plants redifferentiated from the calluses of non-transgenic rice plants, when they are allowed to grow in a medium containing galactose. It also shows the maximal length of the shoots (cm). As is apparent from these figures, the effects of galactose for inhibiting the growth of roots and shoots were found to be reduced by the Ps UGE gene. Thus, the Ps UGE gene was found to modify the sugar metabolism of Gramineae plants and to produce galactose tolerant Gramineae plants that can grow with the use of galactose.

EXAMPLE 6

Evaluation of Salt Stress Tolerance of the Transgenic Rice into which the Ps UGE Gene has been Introduced (1) Evaluation Test of Salt Tolerance Scores of the T0 Generation of the Nipponbare Rice Plants into which the Ps UGE Gene has been Introduced The test of salt stress tolerance was carried out in an isolated greenhouse provided in Totsuka-ku, Yokohama, Japan. The test was carried out between July and September, at an average temperature of 29° C. where the highest temperature was 34° C. and the lowest temperature was 26° C., and at an average humidity of 70% to 90%. The photoperiod was 14 hours on average and the luminous intensity was 50,000 lx. Salt stress was applied in the following manner. Three plastic water baths (0.9 m (breadth)×1.5 m (width)×0.15 m (height)) were provided in the isolated greenhouse, and 10-fold-diluted artificial seawater (Japan. Pet Drugs Co., Ltd.) was poured into the baths to a depth of 10 cm. At this point, NaCl concentration was 0.3%, which was confirmed with a salinometer (ES421, Atago). In order to avoid an increase in salt concentration caused by moisture evaporation, salt concentration was measured once a day. When concentration was elevated, it was adjusted to 0.3% with the addition of tap water. A water-jet pump was provided in the bath to circulate water therein and to inhibit salt concentration imbalances.

The T0 generation of Nipponbare plants into which the Ps UGE gene had been introduced were allowed to grow to maturity for 2 months after acclimation in the manner described in Example 3. The grown plants were maintained in culturing pots (15 cm (width)×5.5 cm (depth)×9.5 cm (height)), immersed in a water bath, and then cultured in 10% seawater. The progress of the test is shown in FIG. 12. In the test, 95 plants of the T0 generation were used and 18 non-transgenic plants redifferentiated from the calluses of the control group were used. These plants were prepared in accordance with the method described in Example 3. In order to immerse these plants in the water bath, the water bath was divided into a plurality of sections (57 cm (breadth)×37 cm (width) each), and the position of each plant in the bath was determined using a table of random numbers.

Salt stress tolerance was evaluated in accordance with the method developed by the International Rice Research Institute (IRRI) in the Philippines. The degree of leaf blight was visually inspected in the 10th week, and each plant was scored in accordance with the definitions of scores according to the method of IRRI (Table 2). The results are shown in FIG. 13. White columns represent the scores of non-transgenic Nipponbare plants, and black columns represent the scores of the T0 plants into which the Ps UGE genes had been introduced. The horizontal axis represents scores and the vertical axis represents the ratios of the numbers of plants exhibiting each score in the population. The score distributions of the group into which Ps UGE genes had been introduced became higher, and the median was increased (from 0.46 to 0.52), compared with the group of non-transgenic plants. This significant difference of 5% was obtained as a result of a chi-square test. Thus, improvement in salt tolerance via introduction of the Ps UGE gene was verified.

TABLE 2

Definition of salt tolerance score

| Salt tolerance score | Conditions of rice |
|---|---|
| 3 | Normal growth of seedlings, no sign of leaf blighting |
| 2 | Slight decline in growth, discoloration of leaf apex, and drying of old leaves |
| 1 | Significant decline in growth, discoloration of all leaves, drying of old leaves, and curling of other leaves |
| 0.5 | Significant decline in growth, and discoloration and blighting of all leaves |
| 0 | Death or blighting of seedlings |

(2) Evaluation Test of Salt Stress Tolerance of the F1 Generation Resulting from the Crossing of the T0 Generation of the Ps UGE Transgenic Nipponbare and Koshihikari The T0 generation of Nipponbare plants into which the Ps UGE gene had been introduced, the salt tolerance of which had been improved in (1) above, was crossed with Koshihikari, which has salt tolerance lower than that of Nipponbare, to obtain the F1 generation. Seeds of the F1 generation and seeds of other varieties were sowed in a Jiffy pot (5 cm (breadth)×5 cm (width)×6 cm (height)). Genomic PCR was carried out in the manner described in Example 3 at the bifoliate and trifoliate stages, and plants were classified into an F1 population (F1 Ps UGE+) in which the Ps UGE genes were observed and another F1 population (F1 Ps UGE−) in which no Ps UGE genes were observed. When classifying plants, cells of the Jiffy pots were isolated from each other, and cells of the same population were gathered on a tray.

The F1 population (F1 Ps UGE+) in which the Ps UGE genes had been observed was subjected to a salt tolerance test in comparison with the F1 population (F1 Ps UGE−) in which no Ps UGE genes were observed and the group of non-transgenic rice plants (varieties: Nipponbare, Koshihikari, and IR28). Salt stress was applied to the rice at the bifoliate and trifoliate stages, and stress application was carried out under the same conditions as in (1) above, except that the plants remained in the Jiffy pots and immersed in the water baths in such state. The test was carried out between December and February, at an average temperature of 28° C. where the highest temperature was 32° C. and the lowest temperature was 24° C., and at an average humidity of 60% to 80%. The photoperiod was 9 hours on average and the luminous intensity was 5,000 to 10,000 lx.

The test results are shown in FIG. 14. The growth conditions of the group of transgenic rice plants into which the Ps UGE gene had been introduced became better than those of the group of non-transgenic rice plants (Nipponbare) in the second week. The number of surviving individuals in the group of transgenic rice into which the Ps UGE gene had been introduced was apparently larger than that of the group of non-transgenic rice plants (Nipponbare) from the fourth to the eighth weeks. From the sixth to the eighth weeks, some seed-producing plants were observed in the population of rice plants into which the Ps UGE genes had been introduced (FIG. 14). FIG. 15 shows the conditions of ear emergence of the Ps UGE transgenic rice after being cultured for 6 weeks under salt stress application.

The survival ratio, the blight ratio, the percentage indicating the number of eared plants, and the number of seeds per ear are shown in Table 3. The F1 population (F1 Ps UGE+) in which the Ps UGE genes were observed exhibited a significantly higher survival ratio compared with the control groups, i.e., the F1 population (F1 Ps UGE−) in which no Ps UGE genes were observed, Nipponbare, Koshihikari, and IR28. The number of eared plants was large in the F1 population (F1 Ps UGE+). The survival ratio of any of the control groups was never higher than that of the group F1 Ps UGE+.

Under such conditions, none of the Nipponbare group, the Koshihikari group, or the IR28 group produced seeds (all plants died before seed production). Compared with F1 Ps UGE−, F1 Ps UGE+ contained a significantly larger number of eared plants and had significant effects of imparting salt tolerance to plants to the extent that the rice yield would be increased. This indicates that the Ps UGE genes have effects of imparting salt stress tolerance to such an extent that the rice yield would be increased through a long period of cultivation, in addition to the effects of improving salt stress tolerance in terms of the survival ratio.

TABLE 3

Evaluation of salt stress tolerance of the F1 generation resulting from the crossing of the T0 generation of the Ps UGE transgenic Nipponbare and Koshihikari

| | Lineage or variety | Blight ratio | Survival ratio | Number of plants tested | Number of eared plants (percentage: %) | Number of seeds per ear (minimal-average-maximal) |
|---|---|---|---|---|---|---|
| F1 | PsUGE+ (2 wks) | 6.2 | 93.8 | 81 | — | — |
| F1 | PsUGE+ (4 wks) | 18.5 | 81.5 | 81 | — | — |
| F1 | PsUGE+ (8 wks) | 44.4 | 55.6 | 81 | 44(54.3) | 1-0.6-5 |
| F1 | PsUGE− (2 wks) | 72.3 | 27.7 | 112 | — | — |
| F1 | PsUGE− (4 wks) | 91.0 | 9.0 | 112 | — | — |
| F1 | PsUGE− (8 wks) | 98.2 | 1.8 | 112 | 2(1.8) | 2-4.0-6 |
| — | Koshihikari (2 wks) | 83.3 | 16.7 | 6 | — | — |
| — | Koshihikari (4 wks) | 100.0 | 0.0 | 6 | — | — |
| — | Koshihikari (8 wks) | 100.0 | 0.0 | 6 | 0(0) | — |
| — | Nipponbare (8 wks) | 70.0 | 30.0 | 6 | 0(0) | — |
| — | IR28 (8 wks) | 100.0 | 0.0 | 6 | 0(0) | — |

EXAMPLE 7

Application of Ps UGE Gene as a Selection Marker

The Ps UGE1a/pBI221Hm expression vector was introduced into rice protoplast via electroporation in accordance with the method described in Example 3. Calluses were regenerated from the protoplast and then redifferentiated over a period of 2 to 6 weeks while containing no antibiotic hygromycin. The redifferentiated plants were planted in an antibiotic- and hormone-free medium containing no sucrose and 10 mM to 200 mM galactose (Ko Shimamoto et al., as above, pp. 78-81) and allowed to grow therein for 1 to 2 weeks. Among the 40,000 planted and redifferentiated plants, rooting and active growth were observed in 6 plants. These 6 plants were subjected to genomic PCR to confirm the gene introduction using the sense primer: 5'-ATG AAA AAG CCT GAA CTC AC-3' (SEQ ID NO: 14) and the antisense primer: 5'-CGA ACC CGC TCG TCT GGC TA-3' (SEQ ID NO: 15) of the hygromycin resistant (HPT) gene that is introduced simultaneously with the Ps UGE gene with the internal sequence primers (SEQ ID NOs: 12 and 13) and the expression vector Ps UGE1a/pBI221Hm of the Ps UGE gene that had been introduced (see Example 3 concerning the PCR conditions). As shown in FIG. 16, a 226-bp band of the Ps UGE gene and a 400-bp band of the internal sequence of the hygromycin resistant (HPT) gene were obtained in all the plants.

Through the above experiments, a Gramineae transgenic plant was selected by using the Ps gene derived from a highly safe plant as a marker gene and using galactose, which is a sugar having a slighter influence on human bodies than antibiotics.

EXAMPLE 8

Preparation of Transgenic Plant (*Arabidopsis thaliana*) and Confirmation of Introduced Gene (1) Preparation of Ps UGE Transgenic *Arabidopsis thaliana*

(1-1) Gene Introduction into *Agrobacterium* via Freeze Thawing

The plasmid UGE1a/pBI221Hm prepared in Example 2 was introduced into *Agrobacterium* via freeze thawing. At the outset, 0.5 ml of a bacterial solution of *Agrobacterium tumefaciens* (GV3101 strain) that had been cultured for 24 hours to saturation was added to 50 ml of culture solution (LB medium), and culture was conducted for 8 hours. After the bacteria were collected, 0.1 µg of DNA solution was suspended in 300 µl of YEB medium (5.0 g of beef extract, 5.0 g of polypeptone, 1.0 g of Bact yeast extract, 5.0 g of sucrose, and 0.5 g of $MgSO_4 \cdot 7H_2O$ per 500 ml). The suspension was allowed to stand in liquid nitrogen for 5 minutes and then in a water bath at 37° C. Culture was conducted at 30° C. for 1 hour, the culture solution was applied to an LB agar medium containing kanamycin (final concentration: 50 µg/ml), and culture was continued for 2 nights to select transgenic plants. The developed transgenic colonies were subjected to single-colony isolation, several colonies were picked, and the presence of the plasmid of interest was confirmed via PCR.

(1-2) Culture of *Agrobacterium* for Transformation

A single colony of *Agrobacterium*, for which the introduction of the Ps UGE gene thereinto had been confirmed, was picked, and pre-culture was conducted in 1 ml of LB liquid medium containing kanamycin (final concentration: 50 µg/ml) at 30° C. for about 24 hours. This pre-culture solution (750 µl) was added to 150 ml of LB medium, and culture was further conducted at 30° C. for about 24 hours. Bacteria were collected via centrifugation and resuspended in a solution for infection (½×MS salt, 5% sucrose, 0.05% silwet). The absorbance at 600 nm was measured and was then adjusted to about 0.5. This solution was used for *Arabidopsis thaliana* infection.

(1-3) Transformation of *Arabidopsis thaliana*

*Arabidopsis thaliana* was transformed in the following manner in accordance with the method of immersion under reduced pressure described in Ko Shimamoto and Kiyotaka Okada (edit.), *Shokubutsu saibo kogaku* (Plant Cell Technology) Series, *Moderu Shokubutsu no jikken purotokoru* (Model plant protocol), 2001, pp. 109-113, Shujunsha).

Seeds of commercially available *Arabidopsis thaliana* (variety: Columbia) were sowed in culture soil and then allowed to grow at 23° C. under long-day conditions (for a light period of 14 hours and a dark period of 10 hours). After gemmation, seedlings were adequately thinned out and were then allowed to grow for about 2 to 4 weeks. When the stems had grown to several centimeters, the plants were top pruned.

The aforementioned top-pruned plants were infiltrated with the *Agrobacterium* solution prepared in (1-2) above about 1 week after top-pruning under reduced pressure. The plants were removed from the infiltrate 1 day thereafter and were then allowed to grow for 2 to 3 weeks. T1 seeds were then sampled.

(2) Acquisition of Homozygous Strains of Ps UGE Gene

T1 seeds obtained from the T0 generation were sowed on a ½ MS agar medium containing kanamycin (final concentration: 50 µg/ml) and tolerant strains were selected. The obtained T1 transgenic plants were firmly planted in rock wool and cultured for a 14-hour photoperiod at 24° C. to obtain seeds of the T2 generation. The seeds of the T2 generation were sowed onto a selection medium, the ratio of drug tolerant individuals to drug non-tolerant individuals of the T3 generation was examined, and strains showing the ratio of 3:1 were selected. Thus, homozygous strains were acquired.

(3) Confirmation of Introduced Gene via Genomic Southern Hybridization

The acquired homozygous strains (Ps UGE6-3, Ps 10-1, Ps 11-1, and Ps 15-5) were subjected to genomic Southern hybridization in order to confirm the introduction of the Ps genes. The seeds of the T3 generation, of which genomic DNA was evaluated to be homozygotes, were inoculated to the MS medium, the aerial parts were harvested 2 weeks thereafter, and the products were then preserved in liquid nitrogen. Genomic DNA was extracted from the resulting sample using a Dneasy Kit (Qiagen). DNA (2 µg each) was digested with the restriction enzyme HindIII and electrophoresed on 0.6% agarose gel. The gel was transferred to a membrane in accordance with the conventional technique. As the probe, the kanamycin-tolerant (NPT) gene region of pBI121 labeled with Alphos Direct was used. After hybridization was carried out at 55° C. overnight, washing was carried out twice with a primary wash liquid at 55° C. for 10 minutes, and twice with a secondary wash liquid for 5 minutes. Detection was carried out in accordance with the protocol. The results of genomic Southern hybridization are shown in FIG. 17 (lane 1: non-transgenic plants; lanes 2 to 5: Ps UGE transgenic plants). It was deduced that lane 2 represents 3 or 4 copies, lanes 3 and 4 represent a single copy, and lane 5 represents 8 or more copies.

(4) Confirmation of Expression of Introduced Gene

RT-PCR was carried out in order to confirm Ps gene expression in the T3 generation. Total RNA was extracted from plants on the plate using the Rneasy Mini Kit (Qiagen). Genomic DNA was digested with RNase-free DNase and removed from total RNA. The resultant was used as a template for cDNA synthesis, a reverse transcriptase was allowed to act using oligo-dT primer, and single-stranded cDNA was synthesized. PCR was carried out using this single-stranded cDNA as a template, and the sequence: 5'-GTG GTC GAC AAC TTC CAC AA-3' (SEQ ID NO: 16) and the sequence: 5'-TTG TTC TCG TAC ATG TA-3' (SEQ ID NO: 17) as primers. PCR was carried out at 98° C. for 2 minutes, for 30 cycles of 95° C. for 30 seconds, 55° C. for 30 seconds, and 72° C. for 1 minute, and 74° C. for 5 minutes. The temperature was then maintained at 4° C. The results of RT-PCR are shown in FIG. 18. The length of the detected fragment was about 250 bp, which was the intended length.

EXAMPLE 9

Confirmation of Galactose Tolerance of Ps UGE Transgenic *Arabidopsis thaliana*

Seeds were obtained from the wild-type *Arabidopsis thaliana*, the pBI121 transgenic *Arabidopsis thaliana*, and the Ps UGE transgenic *Arabidopsis thaliana*. The seeds were sterilized in accordance with a conventional technique and were then sowed on a ½ MS medium with 1% galactose agar, followed by observation of the growth thereof. The results are shown in FIG. 19. While the growth of the wild-type *Arabidopsis thaliana* and that of the pBI121 transgenic *Arabidopsis thaliana* were remarkably inhibited in galactose medium, the growth of the Ps UGE transgenic *Arabidopsis thaliana* was not inhibited.

EXAMPLE 10

Evaluation of Salt Tolerance of Ps UGE Transgenic *Arabidopsis thaliana*

The seeds of the Ps UGE transgenic *Arabidopsis thaliana* were sowed in rock wool and then allowed to grow for a 14-hour photoperiod with 100 µE and a humidity of 60% for 3 weeks. The PNS culture solution was applied at a frequency of once a week. 200 mM NaCl was added 3 weeks later and the culture solutions were exchanged every 3 or 4 days. The growth conditions were also observed every 3 or 4 days. FIG. 20 is a photograph showing the conditions 7 days after salt stress application. As is apparent from the drawing, the rosette leaves of non-transgenic plants underwent complete blight; however, the scapes were extended and seeds were produced in the case of the transgenic *Arabidopsis thaliana*.

EXAMPLE 11

Dicotyledonous plants, i.e., tomatoes, poplars, and Eucalyptuses, are used as examples, and production of transgenic plants therefrom and confirmation of genes introduced thereinto are described.

1. Preparation of Transgenic Plants (1) Preparation of Ps UGE Transgenic Tomatoes Seeds of tomatoes (cultivar: cherry tomatoes, Fukukaen Nursery & Bulb Co., Ltd.) are subjected to surface disinfection with 70% ethanol (for 30 seconds) and 2% sodium hypochlorite (for 15 minutes), transferred to phytohormone-free MS agar medium, and then cultured for a 16-hour photoperiod at 25° C. for 1 week. Cotyledon leaves are cut from the resulting sterilized seedlings, transferred to MS agar medium containing 2 mg/l zeatin and 0.1 mg/l indoleacetic acid (redifferentiation medium, a 9-cm petri dish), and cultured under the same conditions for 2 days. The resultants are used as transgenic materials.

The Ps UGE genes are introduced into *Agrobacterium tumefaciens* individuals (EHA101 strain) in the same manner as in Example 8, and culture is conducted in YEP medium (10 g of bacto-tryptone, 10 g of yeast extract, and 1 g of glucoseper 1,000 ml) overnight. The resulting *Agrobacterium* solution is used as a solution for infection. The cotyledon leaves that has been cultured for 2 days are collected in a sterilized petri dish to be infected with the *Agrobacterium* solution. An excess amount of the *Agrobacterium* solution is removed from the cotyledon leaves using sterilized filter paper, another sheet of sterilized filter paper is placed in the petri dish that has been previously used, in order to inhibit rapid proliferation of *Agrobacterium*, the infected cotyledon leaves are placed thereon, and coculture is conducted for 24 hours.

(2) Preparation of Ps UGE Transgenic Poplar

Poplar (*Populus alba*) leaves are thoroughly washed with a detergent, treated with 1% hypochlorous acid, and washed with sterilized water. The resultants are used as transgenic materials. The *Agrobacterium* solution prepared in the same manner as described above is used as a solution for infection, and transformation is carried out by the leaf disc method in accordance with the procedure specifically described in *Mokuzai Kagaku Kouza* (*Wood Chemistry Lecture*) 11, *Biotechnology*, Kaiseisha Press, p. 42, 2002.

(3) Preparation of Ps UGE Transgenic Eucalyptuses

Leaf sections of 3 mm to 5 mm (excluding leaf stalks) are prepared from in vitro-grown Eucalyptus individuals (*Euca-* lyptus camaldulensis), and the resultants are used as transgenic materials. The same Abrobacterium solution as described above is used as a solution for infection, and transformation is carried out in accordance with the procedure specifically described in Plant Cell reports, 16: 787-791, 1997.

2. Confirmation of Introduced Genes

Leaves (100 mg) are removed from transgenic plants of regenerated plants (i.e., tomatoes, poplars, and Eucalyptuses) and DNA is extracted using a Dneasy kit (Qiagen). PCR is carried out using the extracted DNA as a template and the sequence: 5'-GTG GTC GAC AAC TTC AA-3' (SEQ ID NO: 16) and the sequence: 5'-TTG TTC TCG TAC ATG TA-3' (SEQ ID NO: 17) as primers. PCR is carried out under conditions of 98° C. for 2 minutes, for 30 cycles of 95° C. for 30 seconds, 55° C. for 30 seconds, and 72° C. for 1 minute, and 74° C. for 5 minutes. The temperature is then maintained at 4° C. Gene introduction is confirmed by subjecting the PCR products to agarose gel electrophoresis and detecting the fragments with the lengths of interest.

All publications, patents, and patent applications cited herein are incorporated herein by reference in their entirety.

INDUSTRIAL APPLICABILITY

The present invention provides a gene capable of imparting salt stress tolerance to plants. Introduction of such gene into plants such as rice enables production of salt tolerant plants that can be grown for a long period of time and can produce seeds under an environment where salt stress is applied.

What is claimed is:

1. An isolated polynucleotide encoding the following protein (a), (b), or (c):
   (a) a protein consisting of the amino acid sequence of SEQ ID NO: 2;
   (b) a protein consisting of an amino acid sequence at least 95% homologous to the amino acid sequence of SEQ ID NO: 2 and having activity of imparting salt stress tolerance to plants; or
   (c) a protein consisting of an amino acid sequence at least 95% homologous to the amino acid sequence of SEQ ID NO: 2 and having UDP-glucose 4-epimerase activity.

2. An isolated polynucleotide consisting of the following DNA (d), (e), or (f):
   (d) DNA consisting of the nucleotide sequence of SEQ ID NO: 1;
   (e) DNA encoding a protein consisting of an amino acid sequence at least 95% homologous to the amino acid sequence of SEQ ID NO: 2 and having activity of imparting salt stress tolerance to plants; or
   (f) DNA encoding a protein consisting of an amino acid sequence at least 95% homologous to the amino acid sequence of SEQ ID NO: 2 and having UDP-glucose 4-epimerase activity.

3. A recombinant vector comprising the polynucleotide according to claim 1.

4. A transgenic plant into which the polynucleotide according to claim 1 has been introduced.

5. A salt stress tolerant transgenic plant into which the polynucleotide according to claim 1 has been introduced.

6. The transgenic plant according to claim 4, wherein the plant is monocotyledonous.

7. The transgenic plant according to claim 6, wherein the monocotyledonous plant belongs to the family Gramineae, Liliaceae, or Zingiberaceae.

8. The transgenic plant according to claim 7, wherein the plant that belongs to the family Gramineae is selected from the group consisting of rice, barley, wheat, maize, sugarcane, Zoysia, sorghum, Italian millet, and Japanese millet.

9. The transgenic plant according to claim 4, wherein the plant is dicotyledonous.

10. The transgenic plant according to claim 9, wherein the dicotyledonous plant belongs to the family Brassicaceae, Solanaceae, Leguminosae, Cucurbitaceae, Umbellifera, Asteraceae, Malvaceae, Chenopodiaceae, Myrtaceae, or Salicaceae.

11. A method for imparting salt stress tolerance to plants, which comprises introducing the polynucleotide according to claim 1 into a plant, and expressing a protein encoded by the polynucleotide in the plant.

12. A recombinant vector comprising the polynucleotide according to claim 2.

13. A transgenic plant into which the polynucleotide according to claim 2 has been introduced.

14. A salt stress tolerant transgenic plant into which the polynucleotide according to claim 2 has been introduced.

15. The transgenic plant according to claim 13, wherein the plant is monocotyledonous.

16. The transgenic plant according to claim 15, wherein the monocotyledonous plant belongs to the family Gramineae, Liliaceae, or Zingiberaceae.

17. The transgenic plant according to claim 16, wherein the plant that belongs to the family Gramineae is selected from the group consisting of rice, barley, wheat, maize, sugarcane, Zoysia, sorghum, Italian millet, and Japanese millet.

18. The transgenic plant according to claim 13, wherein the plant is dicotyledonous.

19. The transgenic plant according to claim 18, wherein the dicotyledonous plant belongs to the family Brassicaceae, Solanaceae, Leguminosae, Cucurbitaceae, Umbelliferae, Asteraceae, Malvaceae, Chenopodiaceae, Myrtaceae, or Salicaceae.

20. A method for imparting salt stress tolerance to plants, which comprises introducing the polynucleotide according to claim 2 into a plant, and expressing a protein encoded by the polynucleotide in the plant.

21. A method for imparting salt stress tolerance to plants, which comprises introducing the polynucleotide according to claim 3 into a plant, and expressing a protein encoded by the polynucleotide in the plant.

22. The polynucleotide according to claim 1, wherein said polynucleotide encodes a protein consisting of the amino acid sequence of SEQ ID NO: 2.

23. The polynucleotide according to claim 1, wherein said polynucleotide encodes a protein consisting of an amino acid sequence at least 95% homologous to the amino acid sequence of SEQ ID NO: 2 and having activity of imparting salt stress tolerance to plants.

24. The polynucleotide according to claim 1, wherein said polynucleotide encodes a protein consisting of an amino acid sequence at least 95% homologous to the amino acid sequence of SEQ ID NO: 2 and having UDP-glucose 4-epimerase activity.

25. The polynucleotide according to claim 2, wherein said polynucleotide consists of DNA consisting of the nucleotide sequence of SEQ ID NO: 1.

26. The polynucleotide according to claim 2, wherein said polynucleotide consists of DNA encoding a protein consisting of an amino acid sequence at least 95% homologous to the amino acid sequence of SEQ ID NO: 2 and having activity of imparting salt stress tolerance to plants.

27. The polynucleotide according to claim 2, wherein said polynucleotide consists of DNA encoding a protein consisting of an amino acid sequence at least 95% homologous to the amino acid sequence of SEQ ID NO: 2 and having UDP-glucose 4-epimerase activity.

* * * * *